United States Patent
Kallmyer et al.

(10) Patent No.: US 8,887,619 B2
(45) Date of Patent: Nov. 18, 2014

(54) REMOVABLE HEAT MANAGEMENT FOR RECHARGE COILS

(75) Inventors: Todd A. Kallmyer, Tempe, AZ (US); John E. Kast, Hugo, MN (US); David P. Olson, Minnetrista, MN (US); Randy S. Roles, Elk River, MN (US); Venkat R. Gaddam, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 292 days.

(21) Appl. No.: 13/284,680

(22) Filed: Oct. 28, 2011

(65) Prior Publication Data
US 2013/0105115 A1   May 2, 2013

(51) Int. Cl.
*H02J 7/02* (2006.01)
*A61N 1/36* (2006.01)
*A61N 1/08* (2006.01)
*A61N 1/378* (2006.01)
*A61N 1/375* (2006.01)
*A61N 1/372* (2006.01)

(52) U.S. Cl.
CPC ........... *A61N 1/3787* (2013.01); *A61N 1/37211* (2013.01); *H02J 7/025* (2013.01); *A61N 1/36142* (2013.01); *A61N 1/08* (2013.01); *A61N 1/375* (2013.01)
USPC .......................................................... 92/56

(58) Field of Classification Search
CPC ................... F25D 2400/26; F25D 2303/0822; F25D 2303/085; A62B 17/006; A61F 7/10
USPC ......... 62/259.3, 530; 607/108, 109, 112, 114, 607/115
See application file for complete search history.

(56) References Cited

U.S. PATENT DOCUMENTS

| | | | |
|---|---|---|---|
| 4,226,364 A * | 10/1980 | Utesch | 237/63 |
| 5,884,006 A * | 3/1999 | Frohlich et al. | 392/339 |
| 6,108,489 A * | 8/2000 | Frohlich et al. | 392/346 |
| 6,277,143 B1 * | 8/2001 | Klatz et al. | 607/104 |
| 6,349,234 B2 * | 2/2002 | Pauly et al. | 607/60 |
| 6,384,703 B1 | 5/2002 | Ramos et al. | |
| 6,545,253 B2 * | 4/2003 | Lin et al. | 219/528 |
| 6,699,266 B2 * | 3/2004 | Lachenbruch et al. | 607/96 |
| 6,755,852 B2 * | 6/2004 | Lachenbruch et al. | 607/114 |

(Continued)

FOREIGN PATENT DOCUMENTS

WO   2005037365 A1   4/2005
WO   WO2009/029977   *   3/2009

OTHER PUBLICATIONS

International Search Report and Written Opinion of international application No. PCT/US2012/060406, dated May 7, 2013, 11 pp.

(Continued)

*Primary Examiner* — Mohammad M Ali
(74) *Attorney, Agent, or Firm* — Shumaker & Sieffert, P.A.

(57) ABSTRACT

Devices, systems, and techniques for managing heat generated in coils for wireless energy transmission are disclosed. Inductive coupling between two coils (e.g., a primary coil and a secondary coil) may be used to recharge the power source of an implantable medical device. A phase change material may be thermally coupled to the primary coil to absorb heat generated during the inductive coupling and reduce temperature increases of the primary coil. In one example, the phase change material may be configured to absorb heat from an energy transfer coil. A housing may be configured to contain the phase change material and a coupling mechanism may be configured to removably attach the housing to the energy transfer coil.

31 Claims, 16 Drawing Sheets

(56) References Cited

U.S. PATENT DOCUMENTS

| | | | |
|---|---|---|---|
| 6,852,956 B2 * | 2/2005 | Rock et al. | 219/545 |
| 7,225,032 B2 | 5/2007 | Schmeling et al. | |
| 7,286,880 B2 | 10/2007 | Olson et al. | |
| 7,286,881 B2 | 10/2007 | Schommer et al. | |
| 7,441,558 B2 * | 10/2008 | Leifer et al. | 126/617 |
| 7,505,816 B2 | 3/2009 | Schmeling et al. | |
| 7,512,443 B2 | 3/2009 | Phillips et al. | |
| 7,515,967 B2 | 4/2009 | Phillips et al. | |
| 7,744,640 B1 * | 6/2010 | Faries et al. | 607/109 |
| 7,774,069 B2 | 8/2010 | Olson et al. | |
| 8,326,426 B2 * | 12/2012 | Thornton et al. | 607/36 |
| 2005/0021100 A1 | 1/2005 | Tsukamoto et al. | |
| 2006/0247737 A1 | 11/2006 | Olson et al. | |
| 2006/0247738 A1 | 11/2006 | Schmeling et al. | |
| 2007/0096686 A1 | 5/2007 | Jimenez et al. | |
| 2009/0112291 A1 | 4/2009 | Wahlstrand et al. | |

OTHER PUBLICATIONS

U.S. Appl. No. 13/284,804, filed Oct. 28, 2011, "Heat Management for Recharge Coils for Implantable Medical Devices,".

* cited by examiner

REMOVABLE HEAT MANAGEMENT FOR RECHARGE COILS

TECHNICAL FIELD

The disclosure relates to wireless power transfer for implantable medical devices and, more particularly, to heat management in power transfer coils.

BACKGROUND

Implantable medical devices may be used to monitor a patient condition and/or deliver therapy to the patient. In long term or chronic uses, implantable medical devices may include a rechargeable power source (e.g., one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device.

An electrical current applied to the primary coil generates a magnetic field, and when the primary coil is aligned to the secondary coil, the magnetic field induces an electrical current in the secondary coil within the patient. A charging circuit within the implantable medical device then applies current from the secondary coil to charge the rechargeable power source within the implantable medical device. With transcutaneous transfer via inductive coils, the external charging device does not need to physically connect with the rechargeable power source for charging to occur.

SUMMARY

In general, the disclosure is directed to devices, systems, and techniques for managing heat generated in coils for wireless energy transmission to implantable medical devices. Inductive coupling between two coils (e.g., energy transfer devices) may be used to recharge the power source of an implantable medical device. A primary coil remains external to the patient and a secondary coil may be implanted with the implantable medical device. A phase change material may be thermally coupled to the primary coil to absorb heat generated during the inductive coupling and reduce temperature increases of the primary coil. A coupling mechanism may be provided to removably attach a housing containing the phase change material with the primary coil. In some examples, the phase change material may be contained within thermally conductive tubes or channels configured in shapes that promote flexibility of the housing and contact with the primary coil.

In one aspect, the disclosure is directed to a device that includes a phase change material configured to absorb heat from an energy transfer coil, a housing configured to contain the phase change material, and a coupling mechanism configured to removably attach the housing to the energy transfer coil.

In another aspect, the disclosure is directed to a device that includes means for absorbing heat from an energy transfer coil, means for containing the means for absorbing heat, and means for removably attaching the housing to the energy transfer coil.

In a further aspect, the disclosure is directed to a system that includes an energy transfer coil configured to recharge a rechargeable power source of an implantable medical device and a housing containing a phase change material and configured to be removably attached to the energy transfer coil, wherein the phase change material is configured to absorb heat from the energy transfer coil.

In a further aspect, the disclosure is directed to a method that includes removably attaching a housing to an energy transfer coil, wherein the energy transfer coil is configured to recharge a rechargeable power source of an implantable medical device and the housing contains a phase change material configured to absorb heat from the energy transfer coil.

The details of one or more examples are set forth in the accompanying drawings and the description below. Other features, objects, and advantages will be apparent from the description and drawings, and from the claims.

DETAILED DESCRIPTION

Figure 1:
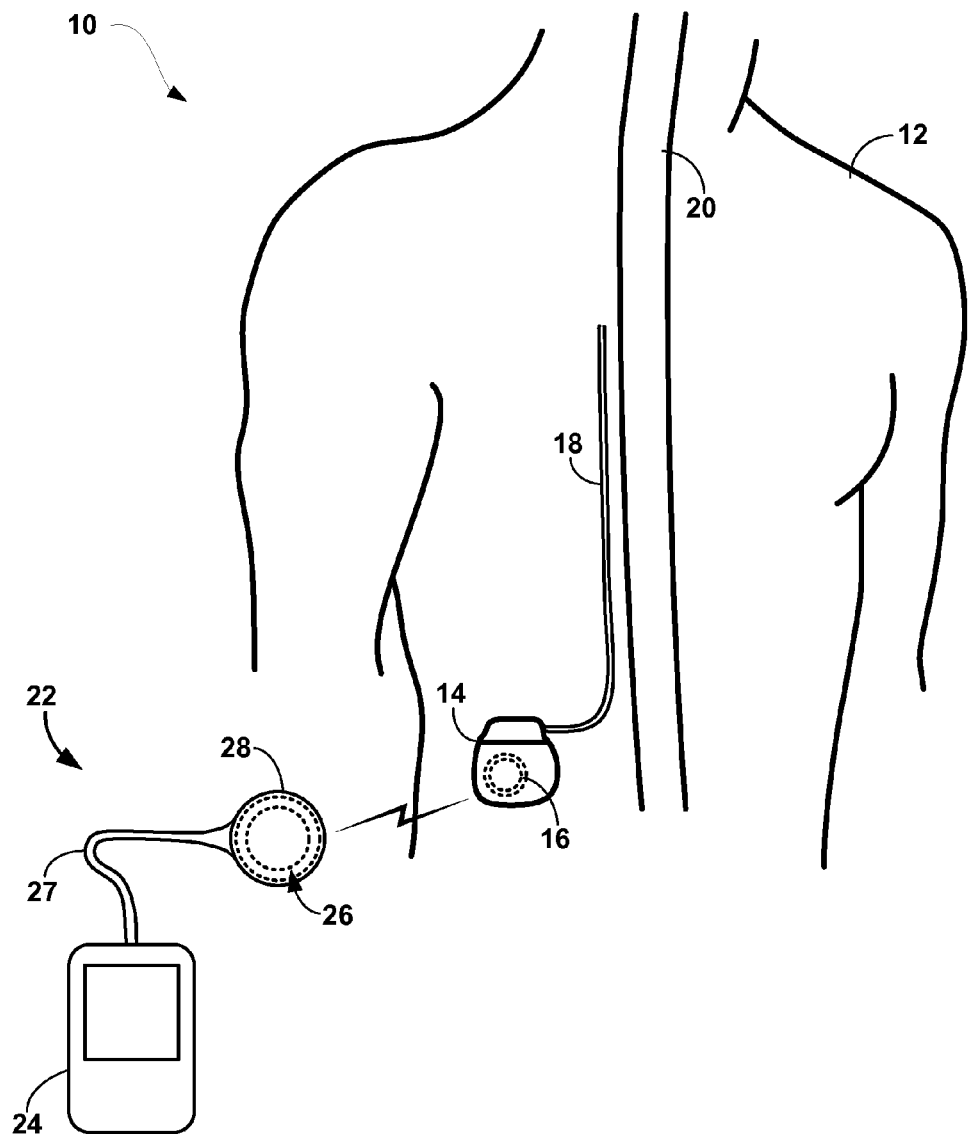
FIG. 1 is a conceptual diagram illustrating an example system that includes an implantable medical device (IMD) and an external charging device that charges a rechargeable power source of the IMD via an energy transfer coil.

This disclosure is generally directed to devices, systems, and techniques for managing heat generated in coils during wireless energy transfer. Typically, inductive coupling, or other wireless energy transfer techniques, may be used to recharge batteries of implantable medical devices (IMDs) and/or transmit information. Inductive coupling may utilize a primary coil of the external charging device to transmit the energy and a secondary coil of the IMD to transcutaneously receive the energy from the primary coil. As an electrical current is generated within the primary coil, the primary coil may increase in temperature, e.g., due to the resistance of the coil. Since the primary coil, and the secondary coil in some examples, may be placed directly against or in close proximity to the skin of the patient, an increase in coil temperature may become uncomfortable for the patient. The coil may be external of the housing of the charging device, or in other examples, the coil may be within the housing of the charging device. The secondary coil of the IMD, however, may be implanted within the patient whether outside or inside of the IMD housing. Not only may these temperatures be uncomfortable, but some patients may prematurely terminate the recharging process or even avoid recharging. Furthermore, some primary coils may be rigid and uncomfortable when forced against the skin of the patient. In other words, the skin of the patient may be deformed by the primary coil during the recharging process, causing discomfort.

As disclosed herein, a heat sink device may generally be removably attached to a primary coil (e.g., an energy transfer coil) used in wireless energy transfer. The heat sink device may include a housing that contains a phase change material configured to absorb heat generated by the energy transfer coil. The removable heat sink device may include a coupling mechanism that facilitates attachment of the heat sink device to the energy transfer coil. For example, the coupling mechanism may include a threaded structure, a retention member, an elastic sheath, or a strap configured to maintain contact between the housing of the heat sink device and the housing of the energy transfer coil. In this manner, the material of both housings may facilitate thermal transfer from the wire of the energy transfer coil to the phase change material within the heat sink device.

The removable feature of the heat sink device may allow a user to add the heat sink device for any time the energy transfer coil may increase in temperature. In other examples, the heat sink device may be configured such that the user may exchange a used (e.g., heated) heat sink device for a new (e.g., cool) heat sink device during a charging session. The heat sink device may thus be used during every charging session of the IMD or only when needed to manage temperature of the energy transfer device. In some examples, the heat sink device and corresponding energy transfer coil may each be constructed to mate together. Alternatively, the heat sink device may be constructed as an aftermarket product to mate with a pre-existing energy transfer coil. The heat sink device may be a permanent, multi-use device that can be used repeatedly by the user. In other examples, the heat sink device may be a single use device, or a limited use device, that is disposable after the user has completed one or more recharge sessions.

In some examples, the heat sink device and contained phase change material may be configured to be flexible and deformable so as to conform to at least a portion of an energy transfer coil configured to deform (e.g., a flexible coil). The flexible coil may conform to non-planar skin surfaces of the patient, and the phase change material may absorb heat generated by the flexible coil. The flexible coil may include insulated wire wound in an in-plane spiral. This in-plane spiral may provide a relatively thin coil that can conform to non-planar surfaces to increase comfort to the patient. The flexible coil may be encased by a flexible housing that protects the flexible coil while also allowing the in-plane spiral of wire to bend and flex out of a single plane. As described herein, the energy transfer coil may be either rigid or flexible. In either case, the heat sink device may be configured to removably attach to the energy transfer coil.

The phase change material generally acts as the heat sink for heat generated by the electrical current in the energy transfer coil. The heat from the energy transfer coil may contribute to the heat of fusion of the phase change material as the phase change material changes from a solid state to a fluid state. During this phase change, the material does not increase in temperature and enables the energy transfer coil to remain at lower temperatures for a longer period of time than otherwise would be possible. In other words, heat generated in the energy transfer coil may be absorbed by the phase change material during the change in phase to limit temperature increases in the energy transfer coil. Example phase change materials may include paraffin waxes (e.g., N-eicosane), fatty acid esters, or other materials with a relatively high heat of fusion and melting points at temperatures appropriate for patient use.

The phase change material may be contained within a housing and, in some examples, within another containment structure (e.g., a thermally conductive elastomer). Although the phase change material may be disposed in a disk-shaped volume with a large surface area to be in thermal communication with the energy transfer coil, the phase change material may alternatively be disposed in structures, locations, or shapes selected to promote or accommodate any flexibility of the energy transfer coil. In other words, the phase change material, and the entire heat sink device, may be configured deform with the energy transfer coil or otherwise accommodate flexibility of at least a portion of the energy transfer coil. In some examples, the flexibility or deformability of the heat sink device may allow a greater surface area of the heat sink device to directly contact the energy transfer coil. This increased contact area may promote thermal communication between the energy transfer coil and the phase change material of the heat sink device.

When in the solid state, the phase change material may not be easily deformable. Therefore, the phase change material may be contained within channels, tubes, beads, or other volumes at predetermined positions within the heat sink device that facilitate flexibility of the heat sink device. Since smaller cross-sectional thicknesses of the phase change material may promote greater bending (e.g., a lower moment of inertia) than larger cross-sectional thicknesses, the configuration of how the phase change material is disposed within the heat sink device may at least partially determine the flexibility, or stiffness, of the heat sink device. In one example, the phase change material may be contained within a plurality of concentric rings on one side of the flexible coil. These configurations (e.g., the volume, shape, and location with respect to the flexible coil) of the phase change material may be selected to accommodate flexibility of the energy transfer coil. In other words, the phase change material may not inhibit, or only minimally inhibit, the flexibility of the energy transfer coil when the heat sink device is removable attached to the energy transfer coil.

The energy transfer coil may also include a flexible housing that encases the wound wire that makes up the coil. The heat sink device may be configured to be disposed on any side of the energy transfer coil. For example, the heat sink may be disposed on the side of the energy transfer coil proximal to patient skin. In other examples the heat sink may be disposed on the side of the energy transfer coil distal to patient skin or on both opposing sides of the energy transfer coil. In some examples, the heat sink device may be configured such that the phase change material may be disposed inside the inner diameter of the in-plane spiral of the coil or outside the outer diameter of the in-plane spiral of the coil. In this manner, the heat sink device may be configured in a variety of different shapes that may facilitate use of the energy transfer coil for charging and managing the temperature of the energy transfer coil.

Although the energy transfer coil is generally described as the primary coil external to the patient, the energy transfer coil could be the secondary coil within the patient to utilize the flexibility and heat management characteristics of the heat sink device described herein. However, the heat sink device may then require a biocompatible housing and removability of the heat sink device may be under-utilized. The flexible nature of some phase change material configurations may allow the heat sink device to be positioned within or adjacent to devices that may include curves or other non-planar surfaces. Portable electronics and devices operating with minimal active cooling features may benefit from a heat sink device as described in this disclosure.

FIG. 1 is a conceptual diagram illustrating example system 10 that includes an implantable medical device (IMD) 14 and an external charging device 22 that charges a rechargeable power source of the IMD 14 via an energy transfer coil 26. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 18 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes a rechargeable power source (not shown) and IMD 14 is coupled to lead 18.

Electrical stimulation energy, which may be constant current or constant voltage based pulses, for example, is delivered from IMD 14 to one or more targeted locations within patient 12 via one or more electrodes (not shown) of lead 18. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 18 is disposed within patient 12, e.g., implanted within patient 12. Lead 18 tunnels through tissue of patient 12 from along spinal cord 20 to a subcutaneous tissue pocket or other internal location where IMD 14 is disposed. Although lead 18 may be a single lead, lead 18 may include a lead extension or other segments that may aid in implantation or positioning of lead 18. In addition, a proximal end of lead 18 may include a connector (not shown) that electrically couples to a header of IMD 14. Although only one lead 18 is shown in FIG. 1, system 10 may include two or more leads, each coupled to IMD 14 and directed to similar or different target tissue sites. For example, multiple leads may be disposed along spinal cord 20 or leads may be directed to spinal cord 20 and/or other locations within patient 12. Lead 18 may carry one or more electrodes that are placed adjacent to the target tissue, e.g., spinal cord 20 for spinal cord stimulation (SCS) therapy.

In alternative examples, lead 18 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 18 and IMD 14 may also be configured to provide other types of electrical stimulation or drug therapy (e.g., with lead 18 configured as a catheter). For example, lead 18 may be configured to provide deep brain stimulation (DBS), peripheral nerve stimulation (PNS), or other deep tissue or superficial types of electrical stimulation. In other examples, lead 18 may provide one or more sensors configured to allow IMD 14 to monitor one or more parameters of patient 12. The one or more sensors may be provided in addition to, or in place of, therapy delivery by lead 18.

IMD 14 delivers electrical stimulation therapy to patient 12 via selected combinations of electrodes carried by lead 18. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 18 is tissue proximate spinal cord 20 (e.g., one or more target locations of the dorsal columns or one or more dorsal roots that branch form spinal cord 20. Lead 18 may be introduced into spinal cord 20 via any suitable region, such as the thoracic, cervical or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 18 may be introduced at any exterior location of patient 12.

Although lead 18 is described as generally delivering or transmitting electrical stimulation signals, lead 18 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 18 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be included, or part of, an external programmer. In this manner, a user may program and charge IMD 14 using one device, or multiple devices.

IMD 14 may be constructed of any polymer, metal, or composite material sufficient to house the components of IMD 14 within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 12 may be configured to provide a hermetic seal for components, such as a rechargeable power source. In addition, the housing of IMD 12 may be selected of a material that facilitates receiving energy to charge a rechargeable power source.

As described herein, secondary coil 16 may be included within IMD 14. However, in other examples, secondary coil 16 could be located external to a housing of IMD 14, separately protected from fluids of patient 12, and electrically coupled to electrical components of IMD 14. This type of configuration of IMD 14 and secondary coil 16 may provide implant location flexibility when anatomical space available for implantable devices is minimal and/or improved inductive coupling between secondary coil 16 and primary coil 26. In any case, an electrical current may be induced within secondary coil 16 to charge the battery of IMD 14 when energy transfer coil 26 (e.g., a primary coil) produces a magnetic field that is aligned with secondary coil 16. The induced electrical current may first be conditioned and converted by a charging module (e.g., a charging circuit) to an electrical signal that can be applied to the battery with an appropriate charging current. For example, the inductive current may be an alternating current that is rectified to produce a direct current suitable for charging the battery.

The rechargeable power source of IMD 14 may include one or more capacitors, batteries, or components (e.g. chemical or electrical energy storage devices). Example batteries may include lithium-based batteries, nickel metal-hydride batteries, or other materials. The rechargeable power source may be replenished, refilled, or otherwise capable of increasing the amount of energy stored after energy has been depleted. The energy received from secondary coil 16 may be conditioned and/or transformed by a charging circuit. The charging circuit may then send an electrical signal used to charge the rechargeable power source when the power source is fully depleted or only partially depleted.

Charging device 22 may be used to recharge the rechargeable power source within IMD 14 implanted in patient 12. Charging device 22 may be a hand-held device, a portable device, or a stationary charging system. In any case, charging device 22 may include components necessary to charge IMD 14 through tissue of patient 12. Charging device 22 may include housing 24 and energy transfer coil 26. In addition, heat sink device 28 may be removably attached to energy transfer coil 26 to manage the temperature of then energy transfer coil during charging sessions. Housing 24 may enclose operational components such as a processor, memory, user interface, telemetry module, power source, and charging circuit configured to transmit energy to secondary coil 16 via energy transfer coil 26. Although a user may control the recharging process with a user interface of charging device 22, charging device 22 may alternatively be controlled by another device (e.g., an external programmer). In other examples, charging device 22 may be integrated with an external programmer, such as a patient programmer carried by patient 12.

Charging device 22 and IMD 14 may utilize any wireless power transfer techniques that are capable of recharging the power source of IMD 14 when IMD 14 is implanted within patient 14. In one example, system 10 may utilize inductive coupling between primary coils (e.g., energy transfer coil 26) and secondary coils (e.g., secondary coil 16) of charging device 22 and IMD 14. In inductive coupling, energy transfer coil 26 is placed near implanted IMD 14 such that energy transfer coil 26 is aligned with secondary coil 16 of IMD 14. Charging device 22 may then generate an electrical current in energy transfer coil 26 based on a selected power level for charging the rechargeable power source of IMD 14. When the primary and secondary coils are aligned, the electrical current in the primary coil may magnetically induce an electrical current in the secondary coil within IMD 14. Since the secondary coil is associated with and electrically coupled to the rechargeable power source, the induced electrical current may be used to increase the voltage, or charge level, of the rechargeable power source. Although inductive coupling is generally described herein, any type of wireless energy transfer may be used to transfer energy between charging device 22 and IMD 14.

Energy transfer coil 26 may include a wound wire (e.g., a coil) (not shown in FIG. 1). The coil may be constructed of a wire wound in an in-plane spiral (e.g., a disk-shaped coil). In some examples, this single or even multi-layers spiral of wire may be considered a flexible coil capable of deforming to conform with a non-planar skin surface. The coil may include wires that electrically couple the flexible coil to a power source and a charging module configured to generate an electrical current within the coil. Energy transfer coil 26 may also include a housing that encases the coil. The housing may be constructed of a flexible material such that the housing promotes, or does not inhibit, flexibility of the coil. Energy transfer coil 26 may be external of housing 24 such that energy transfer coil 26 can be placed on the skin of patient 12 proximal to IMD 14. In this manner, energy transfer coil 26 may be tethered to housing 24 using cable 27 or other connector that may be between approximately a few inches and several feet in length. In other examples, energy transfer coil 26 may be disposed on the outside of housing 24 or even within housing 24. Energy transfer coil 26 may thus not be tethered to housing 22 in other examples.

Heat sink device 28 may be removably attached to energy transfer coil 26. In examples where energy transfer coil 26 is disposed on or within housing 24, heat sink device 28 may be configured to be removably attached to housing 24. Heat sink device 28 may include phase change material that absorbs heat generated in the energy transfer coil 26 during then energy transfer process of a charging session. As charging device 22 generates an electrical current within the energy transfer coil 26, the current may produce heat that increases the temperature of energy transfer coil 26. When energy transfer coil 26 is in close proximity to the skin of patient 12, this increase in temperature may be uncomfortable to patient 12. In other words, energy transfer coil 26 may feel warm to the touch. This increase in temperature may cause patient 12 to shift energy transfer coil 26 to a different location on the skin, remove energy transfer device 26 from the skin, or even discontinue or delay the charging session. Therefore, increased temperatures from energy transfer coil 26 may lead to operational shortcomings of IMD 14, such as reduced operational times between charging sessions due to inadequate charging sessions, in addition to patient discomfort.

The phase change material may be included in heat sink device 28 to manage the temperature of energy transfer coil 26. The phase change material may be any compound or substance selected to change phases (e.g., change from a solid state to a liquid state) at a temperature within the operating temperatures of energy transfer coil 26. Generally, the melting point of the phase change material may be lower than a temperature that would be uncomfortable to patient 12. For example, the phase change material may be selected to have a melting point between approximately 15 degrees Celsius and 50 degrees Celsius. More specifically, the phase change material may have a melting point between approximately 25 degrees Celsius and 45 degrees Celsius. In another example, the phase change material may have a melting point between approximately 35 degrees Celsius and 43 degrees Celsius.

In one example, it may be desirable to limit the temperature of energy transfer coil 26, and the adjacent skin, to be less than or equal to approximately 39 degrees Celsius. Therefore, the phase change material may be selected with a melting point at or near the desired temperature limit. A desired melting point of the phase change material may thus be just below approximately 39 degrees Celsius, such as between approximately 35 degrees Celsius and approximately 38 degrees Celsius. The heat of fusion of the phase change material may thus provide a relatively large heat sink that may help to limit the rise in temperature of the skin above the desired temperature limit. The mass of the phase change material may be selected to achieve desired temperatures of energy transfer device 26. With higher masses of the phase change material, energy transfer coil 26 may remain at the melting point of the phase change material for longer periods of time and limit the temperature of energy transfer coil 26. Without heat sink device 28 attached to (e.g., in thermal communication with) energy transfer coil 26, energy transfer coil 26 may generate undesirable temperatures.

In this manner, heat from energy transfer coil 26 may contribute to the heat of fusion of the phase change material to delay higher temperatures in energy transfer coil 26. After the phase change material has changed to from the solid state to the liquid state, the ability of the phase change material to act as a heat sink may be reduced. However, the phase change material may be subjected to many cycles of changing phases. After the charging session, energy transfer coil 26 will cool along with the phase change material. The phase change material may change back to the solid state from the higher temperature liquid state. Subsequently, the heat of fusion of the phase change material may again function as a heat sink for energy transfer coil 26.

The amount of heat that the phase change material can absorb is also dependent upon the type of material selected, the mass of the material, and degree of thermal communication between the wire of energy transfer coil 26 and the phase change material of heat sink device 28. Although a greater mass of material may absorb a greater amount of heat from energy transfer coil 26, heat sink device 28 may become less flexible with a greater mass of the phase change material. The phase change material may be in thermal communication with energy transfer coil 26 when there is a minimally resistive path for heat between the phase change material and the wound wires of energy transfer coil 26. In this manner, the phase change material may be in thermal communication with energy transfer coil 26 when the housing of heat sink device 28 is disposed in direct contact with the housing of energy transfer coil 26 or separated from energy transfer coil 26 with a thermally conductive material (e.g., a thermally conductive elastomer or a deformable metal alloy). The phase change material may not be considered to be in substantial thermal communication with the coil when an insulator (e.g., a gas, a vacuum, or a thermally insulative material) is disposed between the phase change material to reduce the rate of heat transferred from the coil to the phase change material.

In some examples, two or more different types of phase change materials may be disposed within heat sink device 28. These different materials may be disposed at different locations of heat sink device 28 or commingled across the surface of the housing. Since the different materials may include different melting points and different heats of fusion, the temperature profile of energy transfer coil 26 over time, when heat sink device 28 is attached, may be manipulated. In other words, a phase change material having a lower melting point may delay changes in temperature at a lower temperature while a different phase change material having a higher melting point may delay changes in temperature at a higher temperature. This temperature profile may be selected to provide a more comfortable experience for patient 12. For example, a specific phase change material may be selected to absorb typical temperature spikes during energy transfer, reduce the initial temperature rate increase during energy transfer, and/or reduce the rate of temperature increase near the end of charging sessions.

The phase change material may be selected from any variety of materials having properties sufficient to perform the functions described herein. For example, the phase change material may be a paraffin wax, a fatty acid, ester (carboxylic acid), inorganic materials such as salt hydrates or sodium hydrogen phosphate, or other compounds. The paraffin wax may be a saturated alkane having between 19 and 23 carbon atoms that have approximate melting points in a desired range. Example paraffin waxes may include nonadecane ($C_{19}H_{40}$; approximate melting point of 32.0 degrees Celsius), eicosane or N-eicosane ($C_{20}H_{42}$; approximate melting point of 36.4 degrees Celsius), heneicosane ($C_{21}H_{44}$; approximate melting point of 40.4 degrees Celsius), docosane ($C_{22}H_{46}$; approximate melting point of 44.4 degrees Celsius), or tricosane ($C_{23}H_{48}$; approximate melting point of 47.4 degrees Celsius). In one example, the phase change material selected for heat sink device 28 may include eicosane. In some examples, the phase change material may include both eicosane and heneicosane. In this manner, different phase change materials may be included in heat sink device 28 either in combination or at separate locations in heat sink device 28.

The amount of phase change material included within heat sink device 28 may be selected based on the power transferred by energy transfer coil 26, the material of wire for the coil, the amount of time needed for energy transfer, and the desired temperature limit for energy transfer coil 26. The mass of phase change material needed for energy transfer coil 26 may also be based on the type of material selected. Generally, heat sink device 28 may include between approximately 1.0 gram of phase change material and 100 grams of phase change material. In one example, an heat sink device 28 may include approximately 10 grams of phase change material for an energy transfer coil having a 10 centimeter diameter and a thickness of approximately 4.5 millimeters.

As described herein, heat sink device 28 may include a phase change material configured to absorb heat from energy transfer coil 26. Heat sink device 28 may also include a housing configured to contain the phase change material. In addition, heat sink device 28 may include a coupling mechanism configured to removably attach the housing to energy transfer coil 26. Energy transfer coil 26 may include a rigid or flexible coil of wire. Energy transfer coil 26 may be configured to at least one of transmit energy to or receive energy from secondary coil 16. When heat sink device 28 is removably attached to energy transfer coil 26 (e.g., heat sink device 28 contacts energy transfer coil 26), the phase change material may be in thermal communication with at least a portion of the coil such that the phase change material is configured to absorb heat from the flexible coil. The phase change material (e.g., any material selected to change phases at a temperature generated by the flexible coil) may be a means for absorbing heat from energy transfer coil 26. The housing of heat sink device 28 may be a means for containing the phase change material, and the coupling mechanism may be at least part of a means for removably attaching heat sink device 28 to energy transfer coil 26. In this manner, heat sink device 28 may be selectively attachable and detachable from energy transfer coil 26.

Together, system 10 may include energy transfer coil 26 and heat sink device 28. Energy transfer coil 26 may be configured to recharge a rechargeable power source of IMD 14. Heat sink device 28 may include a housing that contains a phase change material. The housing may be configured to be removably attached to energy transfer coil 26. In this manner, the system may operate such that energy transfer coil 26 generates heat during a recharge session and the phase change material of heat sink device 28 absorbs at least a portion of the generated heat. When the phase change material is at the melting temperature, the heat may contribute to the heat of fusion of the phase change material and not to increasing the temperature of energy transfer coil 26.

The coupling mechanism may be configured to retain at least a portion of the housing in thermal communication with a surface of energy transfer coil 26. When the coupling mechanism is engaged, the housing of heat sink device 28 may be in thermal communication (e.g., direct contact or contact via a thermally conductive material) with the surface of energy transfer device 28. In some examples, energy transfer coil 26 may include a first portion of the coupling mechanism and heat sink device 28 may include a second portion of the coupling mechanism. In other examples, either energy transfer coil 26 or heat sink device 28 may include the entire coupling mechanism for removably attaching heat sink device 28 to energy transfer coil 26. The coupling mechanism may be molded or formed of the housing or, alternatively, attached to the housing. In any case, the coupling mechanism may enable heat sink device 28 to be attached to energy transfer coil 26 and removed from energy transfer coil 26.

In one example, the coupling mechanism may include a threaded structure of heat sink device 28 configured to mate to a threaded surface of energy transfer coil 26. The threaded structure may be a threaded shaft or other bolt-like structure. The threaded surface of energy transfer coil 26 may be configured to mate with the threaded structure of heat sink device 28. Although only one threaded structure and corresponding threaded surface may be used to removably attach heat sink device 28 to energy transfer coil 26, two or more threaded mating structures and surfaces may be used in other examples. Alternatively, the threaded structure of heat sink device 28 may be formed on the outer circumference of the heat sink device housing and configured to mate with a threaded surface of the housing of energy transfer coil 26. In this case, heat sink device 28 may be rotated with respect to energy transfer coil 26 to removably attach heat sink device 28 to energy transfer coil 26.

In another example, the coupling mechanism may include at least one retaining member that extends away from the housing of heat sink device 28 and shaped to retain energy transfer coil 26 between the at least one retaining member and heat sink device 28. The at least one retaining member may be a flange, bent arm, or other member configured to be disposed around at least a portion of energy transfer coil 26. Energy transfer coil 26 may slide within the retaining member to removably attach heat sink device 28. Alternatively, the retaining member may elastically deform when energy transfer coil 26 is attached to heat sink device 28 such that the retaining member snaps around energy transfer coil 26.

In yet another example, the coupling mechanism may include an elastic sheath configured to retain the housing of heat sink device 28 in thermal communication with energy transfer coil 26. The elastic sheath may be formed as a pouch or pocket configured to enclose at least a portion of both heat sink device 28 and energy transfer coil 26. Although both heat sink device 28 and energy transfer coil 26 may be removed from the elastic sheath, either heat sink device 28 or energy transfer coil 26 may be formed within the elastic sheath. The elastic sheath may be constructed of an elastic woven material, an elastic polymer, or other material capable of elastic deformation.

Coupling mechanisms may be disposed on heat sink device 28 and/or energy transfer device 26. Therefore, the coupling mechanism may be reversed between that of heat sink device 28 and energy transfer device 26. In alternative examples, the coupling mechanism may take the form of any device or material that may retain heat sink device 28 against energy transfer coil 26 for a period of time. For example, the coupling mechanism may include a strap, elastic band, hook and loop closures, clamshell housing, partial polymer overmold, removable adhesive, or removable tape. In each of these example coupling mechanisms, the materials and/or configurations of the coupling mechanism may be selected to minimize any interference with thermal communication between heat sink device 28 and energy transfer device 26. The coupling mechanism may include corresponding, e.g., reciprocal, protrusions and recesses in heat sink device 28 and energy transfer coil 26 configured to mate and limit relative movement between the heat sink device and the energy transfer coil.

In some examples, the phase change material of heat sink device 28 may be disposed in one or more shapes selected to accommodate flexibility of energy transfer coil 26 and disposed at one or more positions within heat sink device 28. In other words, the pattern, shape, and volume of the phase change material may be configured to promote flexibility of heat sink device 28 in one or more directions and to the same degree as that of the coil (e.g., the phase change material may be configured to deform with energy transfer coil 26). In this manner, the phase change material size and/or shape may not inhibit (or only minimally inhibit) flexibility of the flexible coil. This configuration of the phase change material may be directed to when the phase change material is in the solid state (e.g., when temperatures of energy transfer device 26 below the melting point of the phase change material). Alternatively, the flexibility of heat sink device 28 due to the configuration of the phase change material may allow heat sink device 28 to conform to the shape of energy transfer coil 26 and create a greater contact area that promotes thermal communication. In this manner, the phase change material may be disposed in at least one shape configured to conform to at least one of energy transfer coil 26 and a non-planar skin surface of patient 12.

Heat sink device 28 and energy transfer device 26 may each also include a flexible housing (not shown in FIG. 1) configured to encase the phase change material and the coil of wire, respectively. The flexible housing, e.g., a means for encasing the phase change material or flexible coil, may be constructed of a flexible material that does not restrict the flexibility of the phase change material or coil. In other words the flexible housing may have an elasticity greater than or equal to the elasticity of the phase change material or coil. Thus, in some examples, heat sink device 28 and/or energy transfer coil 26 may be configured to conform to a non-planar skin surface.

The flexible housing of both heat sink device 28 and energy transfer coil 28 may be constructed of a thermally conductive material to transfer heat between the coil and the phase change material. The thermally conductive material of the flexible housing may include polymers (e.g., thermally conductive elastomers), woven composites, deformable alloys, or other materials that allow the transfer of heat. In some examples, the flexible housing may include one or more channels configured to contain the phase change material. These channels may contain the phase change material to predetermined locations of heat sink device 28 to prevent pooling of the phase change material in the liquid state and retain selected shapes and positions of the phase change material in the solid state.

In some examples, heat sink device 28 may include a containment structure comprising one or more channels configured to contain the phase change material. The containment structure may then be encased by the flexible housing. The channels, in some examples, may be configured as a plurality of cavities that each contain a portion of the phase change material. The containment structure may include two mating portions that are filled with the phase change material and, when combined, contain the phase change material in the channels of the two mating portions. Alternatively, a film may be applied to a surface of the containment structure to retain the phase change material within the one or more channels of the containment structure. In this example, the film may also be configured to contact the flexible coil and transfer heat to the phase change material. The containment structure may be constructed with a material having elastic properties or with a shape that facilitates bending such that the containment structure also accommodates flexibility of heat sink device 28.

In other examples, heat sink device 28 may include one or more flexible tubes configured to contain the phase change material at predetermined locations within the flexible housing. These predetermined locations may be selected based upon the shape and/or mass of energy transfer coil 26. These flexible tubes may be used to contain the phase change material such that the phase change material is disposed within the one or more flexible tubes. The flexible tubes may be constructed of a polymer with a higher melting point temperature than temperatures to which energy transfer coil 26 would normally be exposed. In one example, the flexible tubes may be constructed of a thermally conductive elastomer. In other examples, the tube used may not be flexible. Although the tube may be rigid or generally inflexible, the shape of the tube may still promote deformation of heat sink device 28 in one or more directions.

Alternatively, or in addition to other containment techniques, heat sink device 28 may include a woven material to limit the movement of fluid state phase change material. The woven material may be constructed of a natural or synthetic fiber that promotes wicking of the phase change material in the liquid state. Instead of pooling within the housing of heat sink device 28, the liquid phase change material may adhere to the woven material. Therefore, the phase change material may be placed in contact with the woven material to retain the phase change material in thermal communication with the housing. Although the woven material may be only encased by the housing, the woven material may also be contained by a bladder, flexible tube, or other cavity.

In another alternative example, the phase change material may be encapsulated in a plurality of beads or capsules distributed within the housing of heat sink device 28. Each of these beads may be isolated locations of phase change material. Each of the beads may include phase change material covered with a thermally conductive material, such as an inert and chemically stable polymer. The beads may promote flexibility of heat sink device 28 because each bead may be a relatively small volume compared with the total volume of heat sink device 28. The beads may be shaped as spheres, ovoids, cubes, or other shapes selected to be contained within the flexible housing of heat sink device 28. The beads may generally have an outside diameter between approximately 20.0 micrometers and 5.0 millimeters. In other examples, the outside diameter of the beads may be smaller than 20.0 micrometers or greater than 5.0 millimeters. The dimensions of the beads may be selected based on the total mass or volume of phase change material required and/or the dimensions of energy transfer device 26.

In some examples, a thermally conductive material may be included between heat sink device 28 and energy transfer coil 26. The thermally conductive material may be configured to be disposed between the housing of heat sink device 28 and the housing of energy transfer coil 26. In addition, the thermally conductive material may be deformable to a surface of energy transfer coil 26 and a surface of the housing of heat sink device 28. In this manner, the thermally conductive material may increase the contact surface area between heat sink device 28 and energy transfer coil 26 such that the heat transfer rate may be increased from energy transfer coil 26 to heat sink device 28.

A flexible coil of energy transfer coil 26 may be formed by one or more coils of wire. In one example the coil is formed by a wire wound into a spiral within a single plane (e.g., an in-plane spiral). This in-plane spiral may be constructed with a thickness equal to the thickness of the wire, and the in-plane spiral may be capable of transferring energy with another coil. In other examples, the coil may be formed by winding a coil into a spiral bent into a circle. However, this type of coil may not be as thin as the in-plane spiral.

In one example, the phase change material may be disposed in a disk-shaped volume in a plane. The disk-shaped volume of phase change material may be a solid volume of phase change material approximately the same diameter of the in-plane spiral of energy transfer coil 26 and in a plane parallel with energy transfer coil 26 when heat sink device 28 is removably attached to energy transfer coil 26. The phase change material may alternatively be disposed in a plurality of concentric rings within the housing. However, the phase change material may instead be formed as a spiral tube of phase change material.

In other examples, the phase change material may be disposed in a zigzag pattern within the housing of heat sink device 28. The zigzag pattern may have radial, circumferential, or transverse sections to create the zigzag pattern. These zigzag patterns may be configured to promote curvature of heat sink device 28 in predetermined directions (e.g., radial curvature, circumferential curvature, or transverse curvature). In other examples, the phase change material may be disposed in a plurality of cavities. In another example, the phase change material may be disposed as a coil or rings inside the inner diameter of energy transfer coil 26 and/or outside the outer diameter of energy transfer coil 26.

Although heat sink device 28 may only be configured to be removably attached to one side of energy transfer coil 26, multiple heat sink devices or a heat sink device of a surrounding shape may be disposed on opposing sides, e.g., both sides, of energy transfer coil 26 in other examples. The configuration of phase change material within one heat sink device disposed on one side of energy transfer coil 26 may vary from the configuration of phase change material within another heat sink device disposed on the other side of energy transfer coil 26. These different configurations of phase change material may be selected for heat sink device 28 to be placed between energy transfer coil 26 and skin or for heat sink device 28 to be placed on the non-skin side of energy transfer coil 26. In addition, the thickness and/or mass of phase change material may be varied from one heat sink device to another. In this manner, heat sink device 28 may be positioned next to skin of patient 12 or opposite of the skin of patient 12.

Figure 2A:
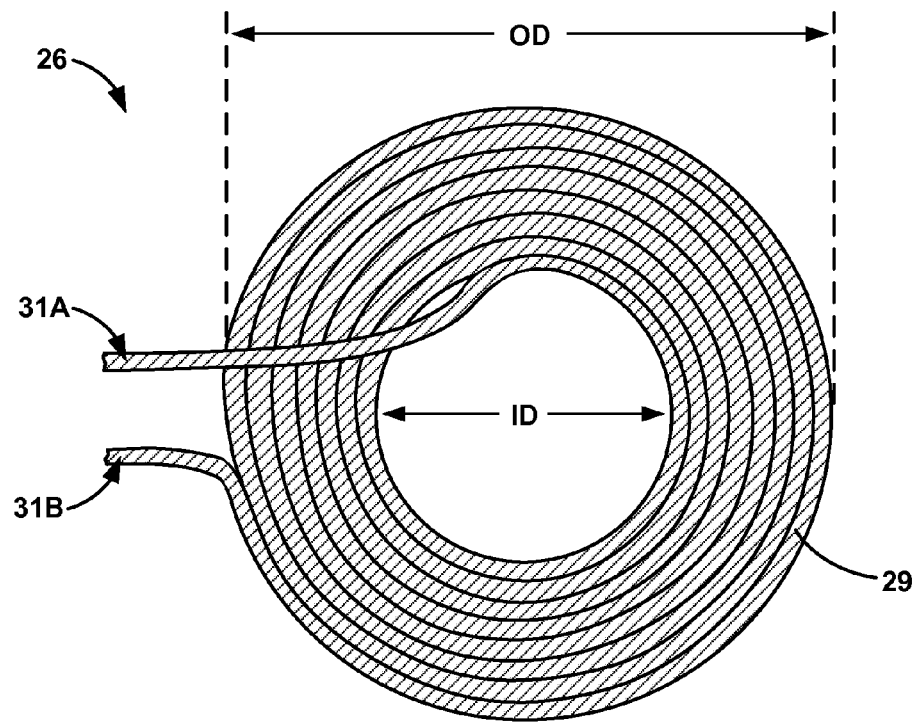
FIG. 2A is a conceptual diagram of an example wound wire of an energy transfer coil.

FIG. 2A is a conceptual diagram of an example wound wire 29 of energy transfer coil 26 of FIG. 1. Energy transfer coil 26 is shown without the flexible housing to illustrate example windings of wire 29 into a spiral, e.g., an in-plane spiral, with an inner diameter (ID) and an outer diameter (OD). Wire 29 may have a selected number of turns directed to the characteristics of energy transfer with another coil, e.g., secondary coil 16 of IMD 14. In general, wire 29 may have as few as 2 turns and as many as several hundred turns to create energy transfer coil 26. Energy transfer coil 26 may electrically couple to a charging module of charging device 22 with wire ends 31A and 31B that may be of any length as needed to couple with the charging module. Although wire 29 may be wound in a single layer, other examples of energy transfer coil 26 may include two or more layers of wire 29 wound in a spiral or circle. Energy transfer coil 26 with multiple layers of wire 29 may also be considered to be an in-plane spiral if wire 29 is spiral wound.

Wire 29 may be constructed of any electrically conductive material sufficient to transfer energy during inductive coupling, for example. Example materials for wire 29 may include copper, silver, gold, aluminum, nickel, or some alloy of two or more materials. Wire 29 may generally have a thickness between approximately 0.5 millimeters (mm) and 10 mm. In one example, wire 29 may have a thickness of approximately 4.5 mm. In general, the OD of energy transfer coil 26 may be between approximately 2.0 centimeters (cm) and 25 cm. The ID of energy transfer coil 26 may generally be between approximately 0.5 cm and 20 cm. In one example, energy transfer coil 26 may have an OD of approximately 10 cm and an ID of approximately 5 cm. In other examples, the dimensions of energy transfer coil 26 and wire 29 may be outside of these ranges for certain applications. In some examples, wire 29 may be covered in insulation that coats the wire. In this manner, insulation may reduce electrical current transfer between adjacent windings of wire 29.

Figure 2B:
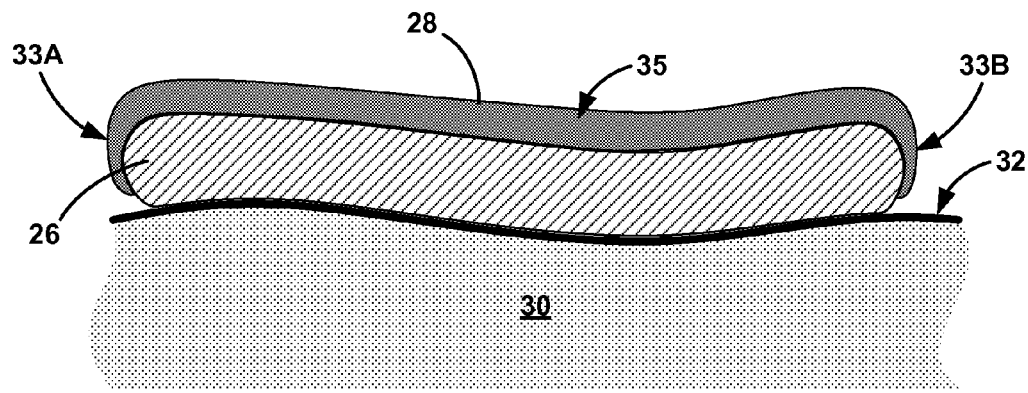
FIG. 2B is a conceptual diagram of an example energy transfer coil of FIG. 1 and conformable housing containing a phase change material in conjunction with a non-planar surface.

FIG. 2B is a conceptual diagram of example energy transfer coil 26 of FIG. 1 and flexible (e.g., conformable) housing 35 containing a phase change material in conjunction with non-planar skin surface 32. As shown in FIG. 2B, skin 30 includes a skin surface 32 that may not be in a single plane. In other words, skin surface 32 may have undulations, curves, and other non-flat surfaces. Therefore, energy transfer coil 26 may be flexible such that the coil can conform to skin surface 32. An in-plane spiral of wire 29, as shown in FIG. 2A of energy transfer coil 26, may allow energy transfer coil 26 to bend and flex as needed.

In this manner, the energy transfer coil 26 may be configured to conform to non-planar skin surface 32. The flexible housing of energy transfer coil 26 may also be configured to deform with the coil. In addition, heat sink device 28 may include flexible housing 35 to deform with energy transfer coil 26. The phase change material within heat sink device 28 may be disposed in one or more shapes selected to accommodate flexibility of energy transfer coil 26. Flexible housing 35 may also include retaining members 33A and 33B for removably attaching heat sink device 28 to energy transfer coil 26. Retaining members 33A and 33B may be similar to retaining members 214A and 214B of FIGS. 12A and 12B. In this manner, the coupling mechanism of retaining members 33A and 33B may partially surround energy transfer coil and retain the phase change material in thermal communication with energy transfer coil 26. Retaining members 33A and 33B may snap in place around the circumferential edge of energy transfer coil 26 or otherwise bend to accept energy transfer coil 26 and exert a force against energy transfer coil 26.

Figure 3A:
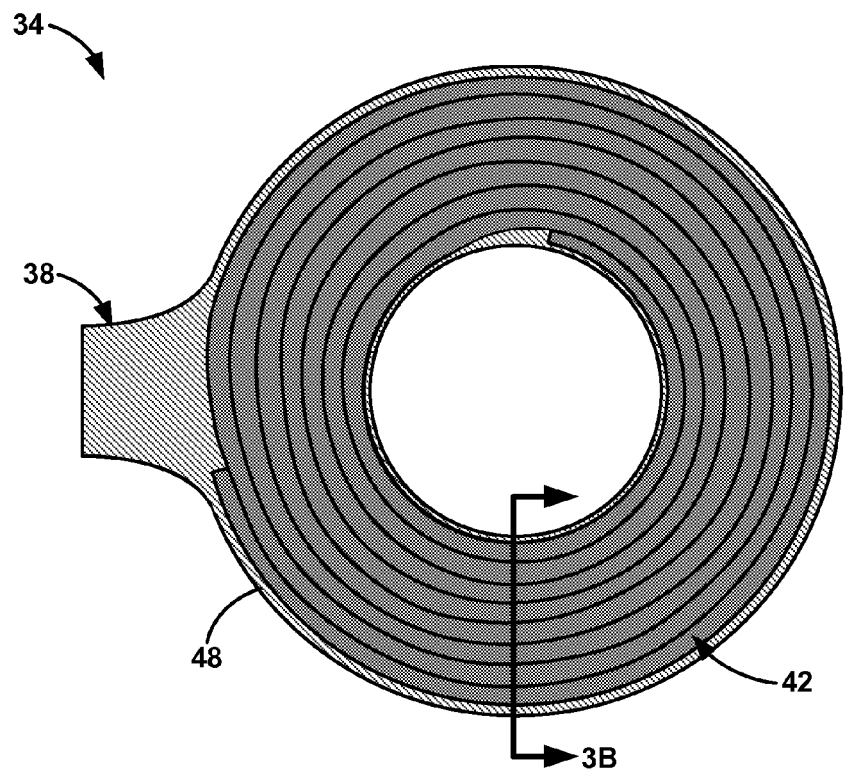
FIGS. 3A and 3B are cross-sectional top and side views of phase change material disposed in a phase change material spiral in conjunction with an energy transfer coil.

FIGS. 3A through 10B illustrate example configurations of phase change material within a heat sink device and the relationship between the heat sink devices and energy transfer coils. However, no coupling mechanisms are provided in FIGS. 3A through 10B for ease of illustration. Instead, FIGS. 11A through 16B provide example coupling mechanisms that could configured to couple any heat sink device to any energy transfer coil. FIGS. 3A and 3B are cross-sectional top and side views of phase change material 42 disposed as a phase change material spiral in conjunction with energy transfer coil 48. Heat sink device 34 is an example of heat sink device 28 of FIG. 1, and energy transfer coil 48 is an example of energy transfer coil 26 of FIG. 1. As shown in FIG. 3A, heat sink device 34 includes phase change material 42. FIG. 3A shows heat sink device 34 with housing 46 removed to expose phase change material 42. Wire coil 40 is shown as a solid component in FIG. 3B for ease of illustration, but wire coil 40 may be an in-plane spiral of multiple wire turns similar to that of energy transfer coil 26 of FIG. 2A. The wire of wire coil 40 may extend from coil 40 to a charging circuit via connector portion 38. In other examples, separate wires may be coupled to coil 40 to transfer or receive electrical current from the charging circuit. Wire coil 40 and the connection of wire coil 40 to a charging circuit may be similar to the energy transfer coils 53, 74, 83, 99, 136, 156, 176, 183, 222, 233, 252, 273, and 293 described herein.

Heat sink device 34 includes phase change material 42 disposed in a continuous spiral. The continuous spiral of phase change material 42 may promote flexibility of heat sink device 34. The continuous spiral of phase change material 42 may also create a large surface area of which may absorb heat from energy transfer coil 48. Although phase change material 42 is shown with eight turns in the spiral, other examples may include fewer or greater numbers of turns. In addition, phase change material 42 may be configured as a single layer spiral, as shown in FIGS. 3A and 3B, or as multiple spiral layers.

Figure 3B:
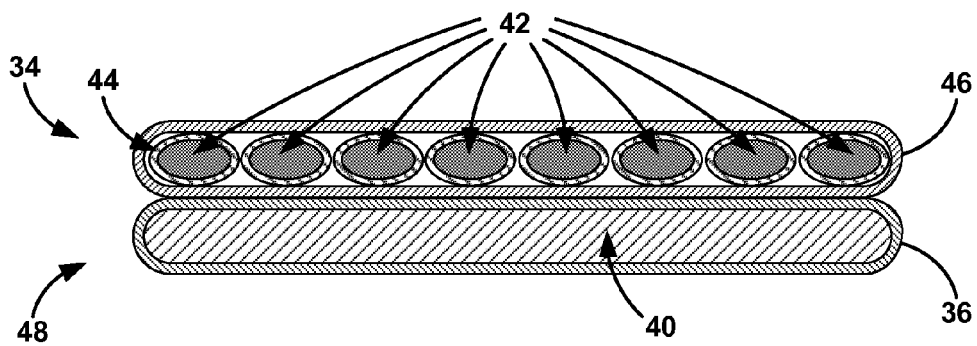

FIG. 3B is an illustration of a cross-section of heat sink device 34 and energy transfer coil 48 indicated by section 3B in FIG. 3A. Flexible coil 40 is shown encased by housing 36. Housing 36 may be rigid or flexible. The thickness of heat sink device 34 may be similar to that of the thickness to that of energy transfer coil 48. For example, the thickness may be between approximately 0.5 millimeters (mm) and 10 mm. In one example, the thickness may be approximately 5.0 mm.

Heat sink device 34 may also include one or more flexible tubes, such as flexible tube 44. Flexible tube 44 may be configured to contain phase change material 42 at the predetermined location within housing 46. In this manner, phase change material 42 may be disposed within flexible tube 44 such that flexible tube 44 may be a casing for the phase change material. Flexible tube 44 may be constructed of a thermally conductive elastomer that is chemically inert to phase change material 42 and chemically stable. Flexible tube 44 may function to retain phase change material 42 if phase change material 42 changes to the liquid state. In addition, housing 46 that encases phase change material 42 and flexible tube 44 may be rigid or flexible.

In some examples, heat sink device 34 may include a woven material placed in contact with phase change material 42. The woven material may be used to retain phase change material 42 in thermal communication with housing 46 because the phase change material 42 may wick to the woven material when in the liquid state. This woven material may be used in addition to, or instead of, flexible tube 44.

In other examples, heat sink device 34 may incorporate phase change material 42 encapsulated in a plurality of beads distributed within housing 46. These beads of phase change material may be disposed in a single plane or in a greater volume of housing 46. The individual beads may take the place of the tubes of phase change material. Each of the beads may include a polymer coating around phase change material 42 to retain the phase change material in the shape of the bead. In this manner, both flexible tube 44 and beads may be means for containing phase change material 42 at predetermined locations within housing 46. In alternative examples, housing 46 may include ridges or channels that extend across the thickness of heat sink device 34 to functionally contain phase change material 42 within predetermined locations of heat sink device 34.

Figure 4A:
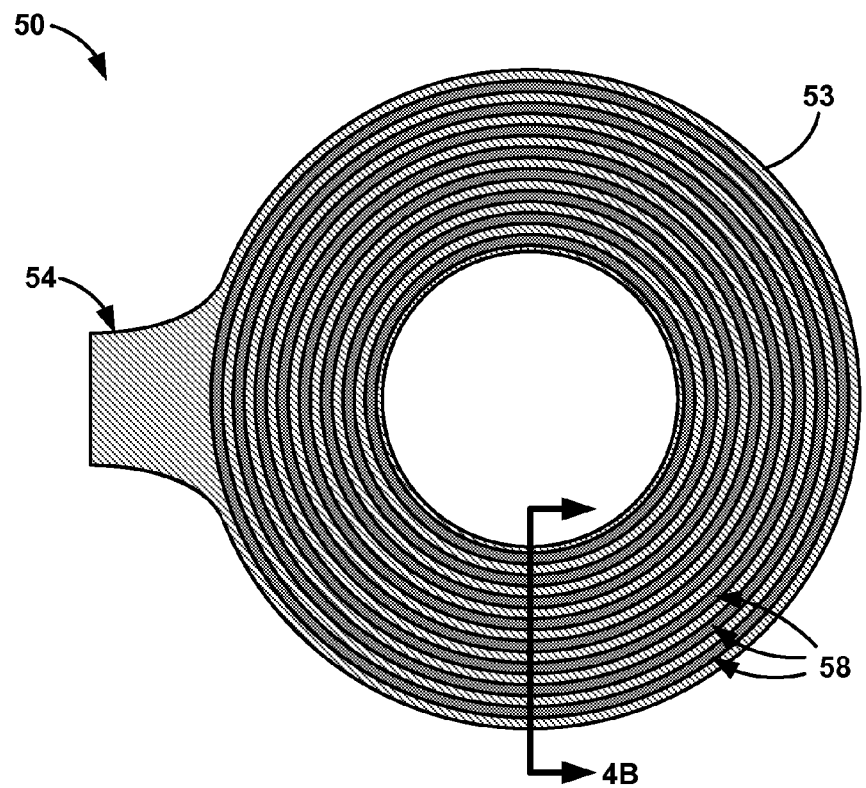
FIGS. 4A and 4B are cross-sectional top and side views of a phase change material disposed in a plurality of concentric rings in conjunction with an energy transfer coil.
Figure 4B:
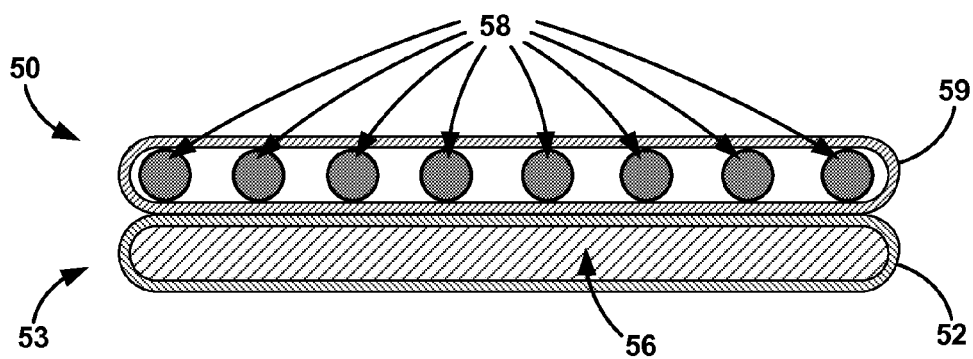

FIGS. 4A and 4B are cross-sectional top and side views of phase change material 58 disposed in a plurality of concentric rings in conjunction with energy transfer coil 53. Heat sink device 50 is an example of heat sink device 28 of FIG. 1, and energy transfer coil 53 is an example of energy transfer coil 26 of FIG. 1. As shown in FIG. 4A, heat sink device 50 includes phase change material 58. FIG. 4A shows heat sink device 50 with housing 59 removed to expose phase change material 58. Wire coil 56 is shown as a solid component in FIGS. 4A and 4B for ease of illustration, but wire coil 56 may be an in-plane spiral of wire similar to that of wire 29 of FIG. 2A.

Heat sink device 50 includes phase change material 58 disposed in a plurality of concentric rings in a single plane. The concentric rings may be separated (e.g., by a void or other material) or in contact with each other. The concentric rings of phase change material 58 may reside against housing 59 to promote thermal communication between housing 59 and energy transfer coil 53 and phase change material 58. In the example of FIG. 4A, heat sink device 50 includes eight rings of phase change material 58. Phase change material 58 may be disposed in as few as one ring in another example or as many as 20 or more concentric rings on other examples. Multiple heat sink devices 50 may be disposed on one side of energy transfer coil 53 or on both opposing sides of energy transfer coil 53 in other examples.

FIG. 4B is an illustration of a cross-section of heat sink device 50 indicated by section 4B in FIG. 4A. Heat sink device 50 is shown with phase change material 58 within and encased by housing 59 and adjacent to energy transfer coil 53. The thickness of heat sink device 50 may be similar to the thickness of the wire in coil 56, but the thickness of heat sink device 50 may be less or greater in other examples. Although the spaces between the rings of phase change material 58 may be filled with air or other gas, the spaces may instead be filled with a thermally conductive fluid or deformable material. Housing 52 of energy transfer device 53 encases coil 56.

Similar to heat sink device 34 of FIG. 3B, heat sink device 50 may also include one or more flexible tubes, beads, or a woven material to contain phase change material 58 at predetermined locations within housing 59. In some examples, housing 59 may include one or more channels configured to contain phase change material 58. The channels may be formed by ridges that extend inward. In other examples, heat sink device 50 may include a containment structure that includes one or more channels configured to contain phase change material 58. A film may then be applied to a surface of the containment structure to retain phase change material 58 within the one or more channels. The film may be thermally conductive and contact an inner surface of housing 59. Alternative to the film, the containment structure may include multiple portions that separate to receive phase change material 58 and seal to retain the phase change material within heat sink device 50.

Figure 5A:
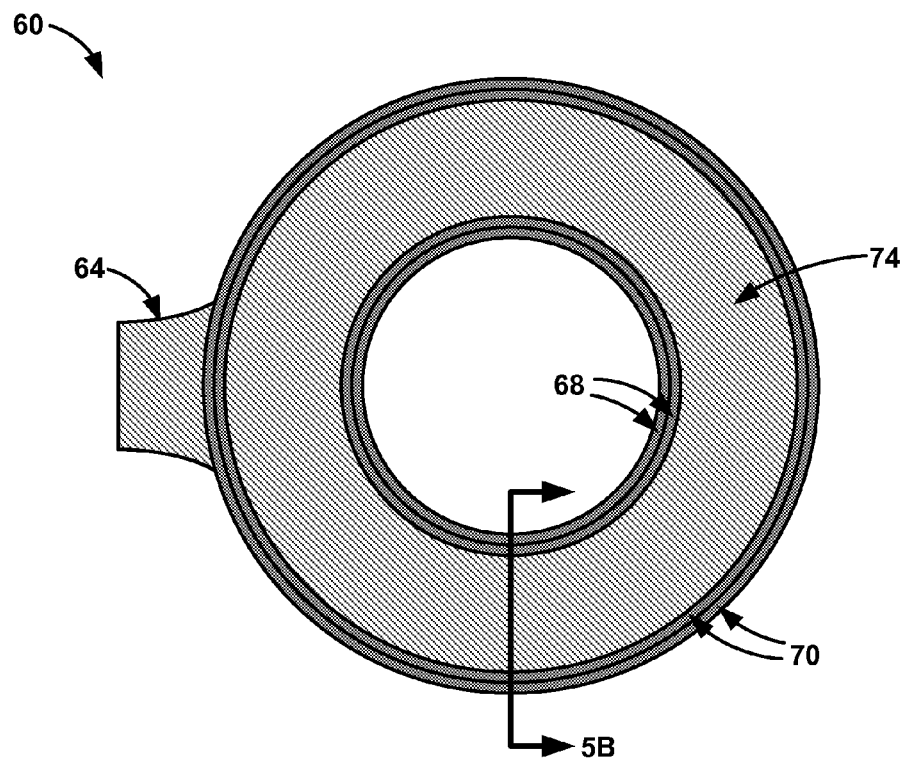
FIGS. 5A and 5B are cross-sectional top and side views of a phase change material disposed inside an inner diameter and outside an outer diameter of an energy transfer coil.
Figure 5B:
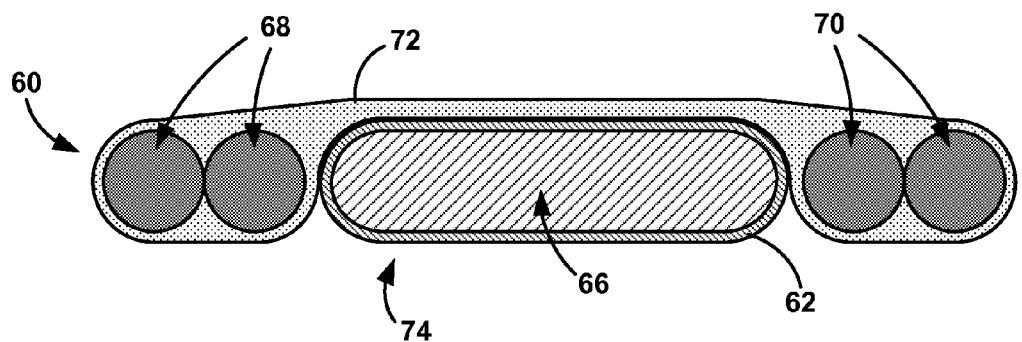

FIGS. 5A and 5B are cross-sectional top and side views of phase change material disposed inside an inner diameter and outside an outer diameter of energy transfer coil 74. Heat sink device 60 is an example of heat sink device 28 of FIG. 1, and energy transfer coil 74 is an example of energy transfer coil 26 of FIG. 1. As shown in FIG. 5A, heat sink device 60 includes phase change material disposed in inner rings 68 and outer rings 70. Energy transfer coil 74 includes connector portion 54. FIG. 5A shows heat sink device 60 with the top of housing 72 removed to expose the phase change material in inner rings 68 and outer rings 70. Flexible coil 66 is shown as a solid component in FIG. 5B for ease of illustration, but coil 66 may be an in-plane spiral of wire similar to that of energy transfer coil 26 of FIG. 2A.

Heat sink device 60 includes phase change material disposed in a plurality of rings that may be disposed in the same plane as energy transfer coil 74. More specifically, the phase change material is disposed within rings inside the inner diameter of energy transfer coil 74 and outside the outer diameter of energy transfer coil 74. Inner rings 68 include the phase change material disposed inside the inner diameter of energy transfer coil 74. In addition, outer rings 70 include the phase change material disposed outside the outer diameter of energy transfer coil 74. Although FIGS. 5A and 5B illustrates two inner rings 68 and two outer rings 70, other examples of heat sink device 60 may include a single inner ring and a single outer ring, or more than two inner and outer rings. In addition, the number of inner rings 68 may be different than the number of outer rings 70. In other examples, a spiral, or coil, of phase change material may be disposed in place of inner rings 68 and/or outer rings 70.

FIG. 5B is an illustration of a cross-section of heat sink device 60 indicated by section 5B in FIG. 5A. Energy transfer coil 74 includes wire coil 66 within housing 62. Heat sink device 60 is shown with phase change material disposed in inner rings 68 and outer rings 70 to the sides of and adjacent to energy transfer coil 74. Housing 72 is also provided to encase inner rings 68 and outer rings 70. The thickness of heat sink device 60 and attached energy transfer coil 74 may be only slighter greater than the thickness of energy transfer coil 74 because the phase change material is disposed in generally the same plane as energy transfer coil 74.

Similar to heat sink device 34 of FIG. 3B, heat sink device 60 may also include one or more flexible tubes, beads, or a woven material to contain the phase change material if rings 68 and 70 at predetermined locations within housing 72. In some examples, housing 72 may include one or more channels configured to contain the phase change material. In other examples, a containment structure and/or a film may be used to contain the phase change material at the inner and outer diameter locations with respect to energy transfer coil 74.

Figure 6A:
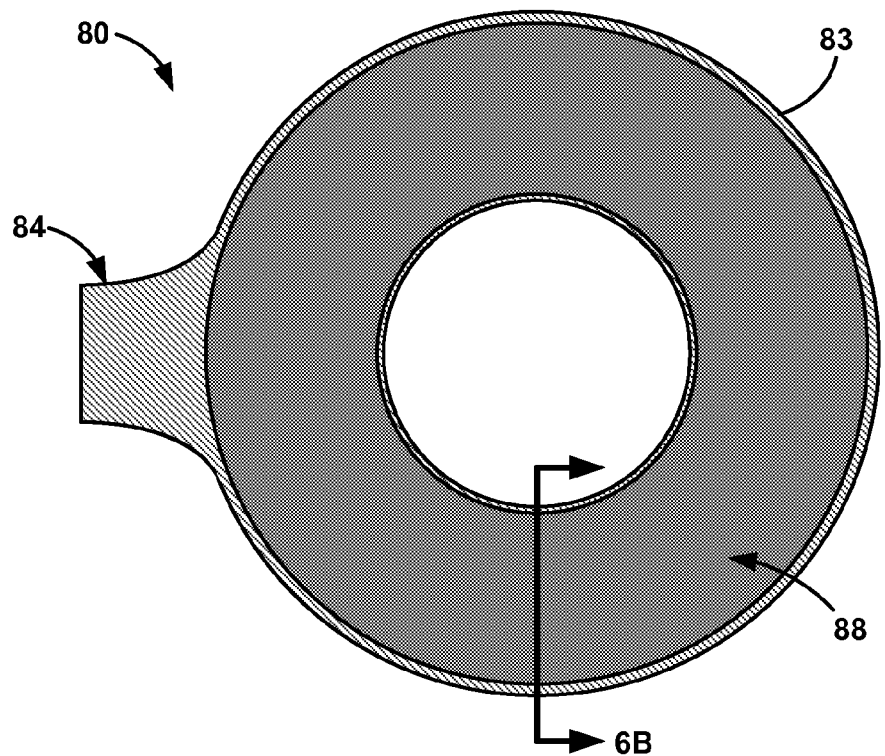
FIGS. 6A, 6B, and 6C are cross-sectional top and side views of a phase change material disposed in a disk-shaped volume in conjunction with an energy transfer coil.
Figure 6B:
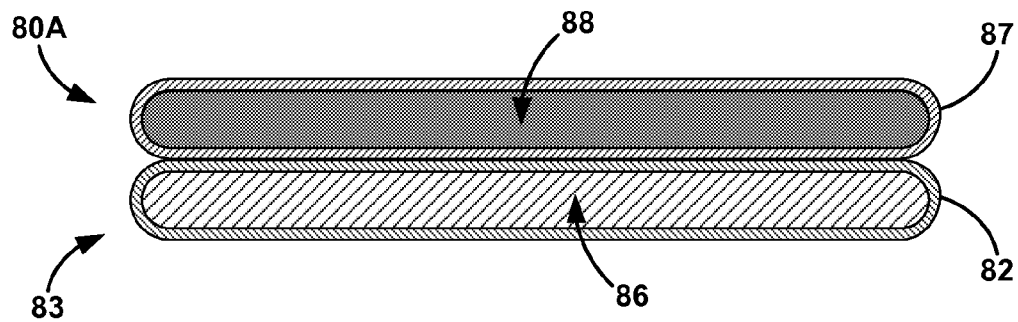
Figure 6C:
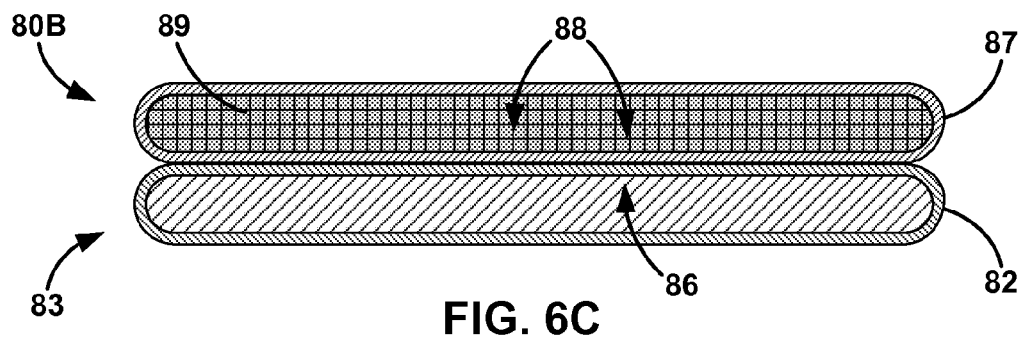

FIGS. 6A, 6B, and 6C are cross-sectional top and side views of a phase change material disposed in disk-shaped volume 88 in conjunction with energy transfer coil 83. Heat sink device 80 is an example of heat sink device 28 of FIG. 1, and energy transfer coil 83 is an example of energy transfer coil 26 of FIG. 1. As shown in FIG. 6A, heat sink device 80 includes phase change material disposed in disk-shaped volume 88 (e.g., a doughnut shaped volume). Energy transfer coil 83 includes coil 86, housing 82, and connector portion 84. FIG. 6A shows heat sink device 80 with housing 87 removed to expose disk-shaped volume 88 of phase change material. Coil 86 is shown as a solid component in FIGS. 6B, and 6C for ease of illustration, but coil 86 may be an in-plane spiral of wire similar to that of energy transfer coil 28 of FIG. 2A.

Heat sink device 80 includes phase change material disposed in disk-shaped volume 88 in a plane that may be placed adjacent and generally parallel to energy transfer coil 83. Disk-shaped volume 88 may be disposed such that the large flat surface area of disk-shaped volume 88 is positioned to contact housing 87 and the flat surface area of energy transfer coil 83. The increased contact area between disk-shaped volume 88 of heat sink device 80 and flexible coil 83 may increase the thermal communication to the phase change material and improve the heat management of energy transfer coil 83. Disk-shaped volume 88 may have a thickness and diameter slightly less than that of energy transfer coil 83. In other examples, disk-shaped volume 88 may have a thickness and diameter equal to or greater than energy transfer coil 83.

FIG. 6B is an illustration of a cross-section of heat sink device 80A indicated by section 6B in FIG. 6A. Heat sink device 80A is one example of disk-shaped volume 88. Heat sink device 80A is shown with phase change material disposed disk-shaped volume 88 encased by housing 87. Heat sink device 80A is also disposed on top of, and adjacent to, energy transfer coil 83. The thickness of heat sink device 80A may be lesser or greater than the thickness of coil 86. Housing 82 is provided by energy transfer coil 83 to encase coil 86.

Similar to heat sink device 34 of FIG. 3B, heat sink device 80A may also include a flexible tube or bladder to contain the phase change material in disk-shaped volume 88. This flexible tube may be a thermally conductive material that is also flexible. In some examples, the flexible tube or bladder may include compartments or sections that prevent movement of the phase change material in the liquid state.

In alternative examples, housing 87 may include one or more channels configured to contain the phase change material or a containment structure and/or a film may be used to contain the phase change material in the disk-shaped volume 88. Housing 87 may then encase the containment structure for disk-shaped volume 88 of the phase change material. In another example, disk-shaped volume 88 may be filled with a plurality of individual beads that each contain phase change material.

FIG. 6C is an illustration of a cross-section of heat sink device 80B indicated by section 6B in FIG. 6A. FIG. 6C may be similar to FIG. 6B; however, heat sink device 80B may also include woven material 89 to retain the phase change material within disk-shaped volume 88. Woven material 89 may be constructed of a natural or synthetic fiber that promotes wicking of the phase change material in the liquid state. Instead of pooling within disk-shaped volume 88 or within housing 87, the liquid phase change material may adhere to woven material 89 via capillary action or other molecular forces. Therefore, the phase change material may be placed in contact with woven material 89 to retain the phase change material in thermal communication with housing 87 and energy transfer coil 83. Although woven material 89 may be only encased by housing 87, woven material 89 may also be contained by a bladder, flexible tube, film, or other cavity.

Figure 7A:
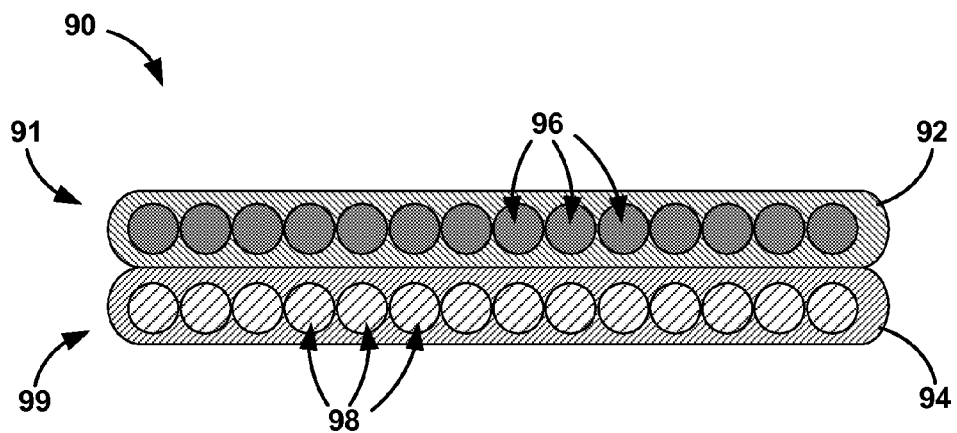
FIGS. 7A and 7B are cross-sectional side views of a phase change material disposed on one side and on an opposing side of an energy transfer coil.
Figure 7B:
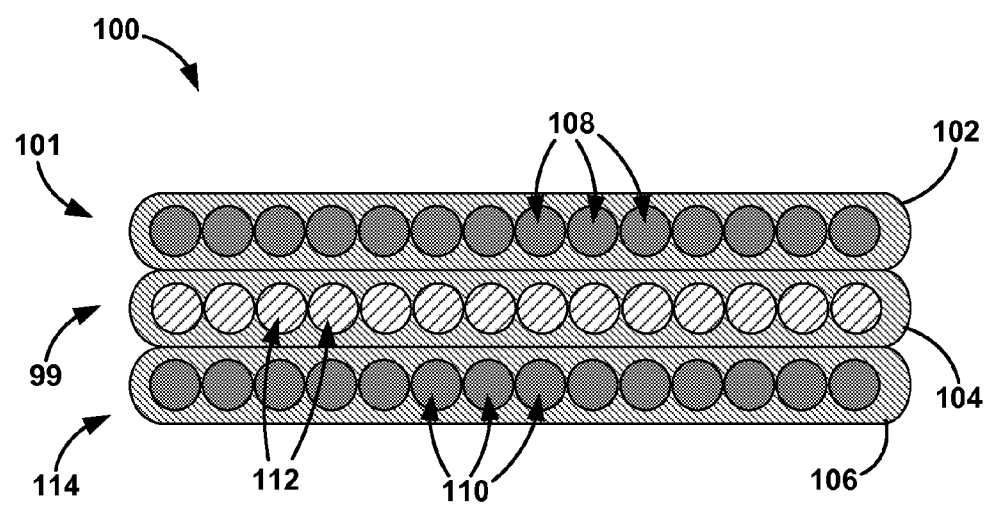

FIGS. 7A and 7B are cross-sectional side views of phase change material 96 disposed on one side and opposing sides of energy transfer coil 112. Heat sink devices 91 and 114 are examples of heat sink device 28 of FIG. 1, and energy transfer coil 99 is an example of energy transfer coil 26 of FIG. 1. As shown in FIG. 7A, heat sink device 91 includes phase change material 96 in a spiral configuration. In addition, heat sink device 91 is removably attached to one side of energy transfer coil 98. In this manner, heat sink device 91 and energy transfer coil 99 may be a part of system 90. In other examples, phase change material 96 may be contained within flexible tubes, channels, beads, or any other containment structure. Wire coil 98 is also shown as an in-plane spiral of wire. Similar to other energy transfer coils described herein, wires may be coupled to opposite ends of the in-plane spiral such that the charging circuit can drive electrical current through wire coil 98. Phase change material 96 may be retained in housing 92 of heat sink device 91, and wire coil 98 may be retained within housing 94 of energy transfer coil 99. Housings 92 and 94 may be formed separately and removably attached with one or more coupling mechanisms. Housings 92 and 94 may also be flexible and/or facilitate thermal communication between wire coil 98 and phase change material 96.

As shown in FIG. 7B, system 100 includes heat sink devices 101 and 114 removably attached to energy transfer coil 99. Heat sink devices 101 and 114 include phase change material 108 and 110 disposed on opposing sides of wire coil 112 (e.g., a coil of multiple turns of wire). Heat sink device 101 includes phase change material 108 in a spiral configuration within housing 102 on one side of energy transfer coil 99. In addition, phase change material 110 is included in a spiral configuration on the opposing side of energy transfer coil 112 within housing 106 of heat sink device 114. Phase change material 108 and 110 may be contained within flexible tubes, channels, beads, or any other containment structure. Wire coil 112 is also shown as an in-plane spiral of wire. Phase change materials 108 and 110 may be retained in housings 102 and 106, respectively. Wire coil 112 may be retained within housing 104. Housings 102, 104, and 106 may include at least part of a coupling mechanism in some examples. Housings 102, 104, and 106 may also be flexible and/or facilitate thermal communication between flexible coil 112 and phase change materials 108 and 110.

In the examples of FIGS. 7A and 7B, phase change materials 96, 108, and 110 may each be contained within channels of the respective flexible housings 92, 102, and 106. These channels may not require the use of any other material to contain or retain the phase change material. However, additional containment structures, e.g., flexible tubes, may also be included within the channels. Although the channels are illustrated with a circular cross-section, the channels may be constructed of any shape. For example, the channels have square, rectangular, oval, or unsymmetrical cross-sections.

Figure 8A:
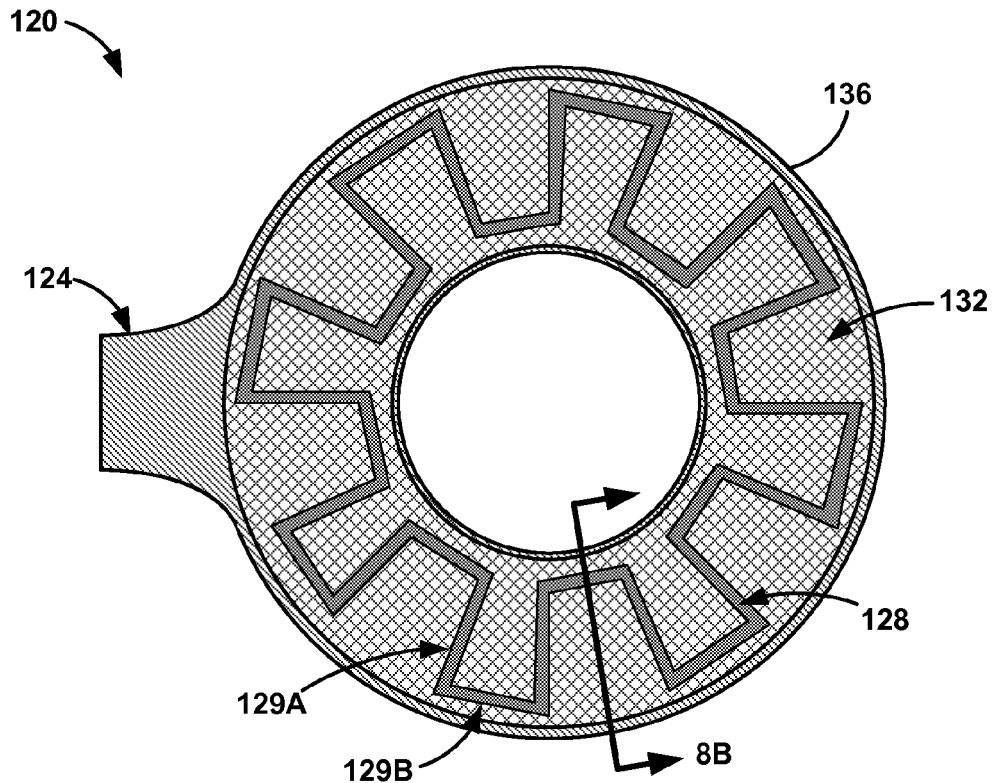
FIGS. 8A and 8B are cross-sectional side views of a phase change material disposed in a radial zigzag pattern in conjunction with an energy transfer coil.
Figure 8B:
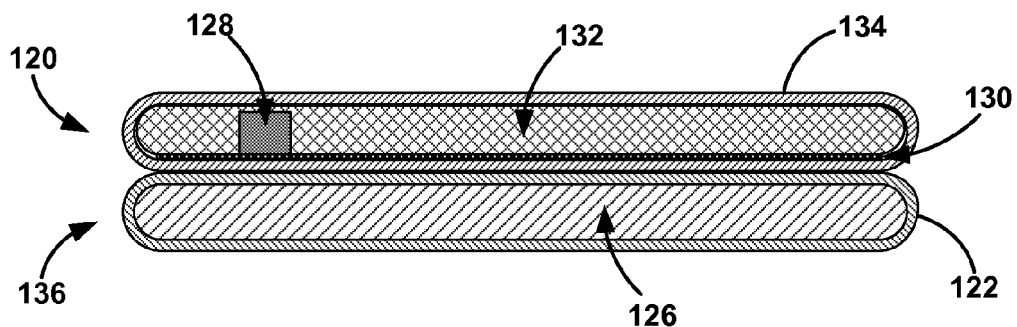

FIGS. 8A and 8B are cross-sectional side views of a phase change material disposed in radial zigzag pattern 128 in conjunction with energy transfer coil 136. Heat sink device 120 is an example of heat sink device 28 of FIG. 1, and energy transfer coil 136 is an example of energy transfer coil 26 of FIG. 1. As shown in FIG. 8A, heat sink device 120 includes phase change material in radial zigzag pattern 128. Energy transfer coil 136 includes connector portion 124 for coupling coil 126 with a charging device. FIG. 8A shows heat sink device 120 with the top of housing 134 removed to expose radial zigzag pattern 128 on top of, or adjacent to, energy transfer coil 136. Wire coil 126 is shown as a solid component in FIG. 8B for ease of illustration, but coil 126 may be an in-plane spiral of wire similar to that of energy transfer coil 26 of FIG. 2A.

Energy transfer device 120 includes phase change material disposed in radial zigzag pattern 128 disposed within a plane. Radial zigzag pattern 128 includes radial sections 129A that extend between the inner and outer diameter of heat sink device 120 and circumferential sections 129B that extend around the circumference of heat sink device 120. This configuration of radial zigzag pattern 128 may be configured to promote curvature of heat sink device 120 in predetermined directions. For example, radial zigzag pattern 128 may promote flexibility or curvature of heat sink device 120 across the circumference of heat sink device 120. In other words, heat sink device 120 may more easily deform at any circumferential position across the center of heat sink device 120.

As shown in FIG. 8A, radial zigzag pattern 128 includes 16 radial segments 129A and 16 circumferential sections 129B. However, radial zigzag pattern 128 may include fewer or greater radial and circumferential sections in other example. A radial zigzag pattern 128 with more segments may increase the mass of phase change material in heat sink device 120 that in turn provides a larger heat sink for energy transfer coil 136. The phase change material in radial zigzag pattern 128 may reside flat within heat sink device 120 to promote thermal communication between energy transfer coil 136 and the phase change material. Radial zigzag pattern 128 may be disposed on one side of energy transfer coil 136 or on both opposing sides of energy transfer coil 136 in other examples.

FIG. 8B is an illustration of a cross-section of heat sink device 120 indicated by section 8B in FIG. 8A. Heat sink device 120 is shown with the phase change material of radial zigzag pattern 128 within housing 134. The thickness of heat sink device 120 may be less than, equal to, or greater than the thickness of the wire in wire coil 126. Housing 122 encases wire coil 126 separate from the phase change material of radial zigzag pattern 128.

Radial zigzag pattern 128 may be formed by channels within containment structure 132. Containment structure 132 may be constructed of a thermally conductive or thermally insulative material that is also flexible. Film 130 may be applied to the surface of containment structure 132 to retain the phase change material within the channels of containment structure 132. Film 130 may be adhered to containment structure 132 with an adhesive or other bonding technique. Film 130 may also be configured to contact housing 134 and transfer heat to the phase change material in radial zigzag pattern 128. Alternatively, containment structure 132 may include two mating portions that are filled with the phase change material and, when combined, contain the phase change material in the channels of the two mating portions.

Similar to heat sink device 34 of FIG. 3B, heat sink device 120 may alternatively include one or more flexible tubes, beads, or a woven material to contain the phase change material in radial zigzag pattern 128 at predetermined locations with in housing 134. In other examples, radial zigzag pattern 128 may be formed in one or more channels or cavities of housing 134.

Figure 9A:
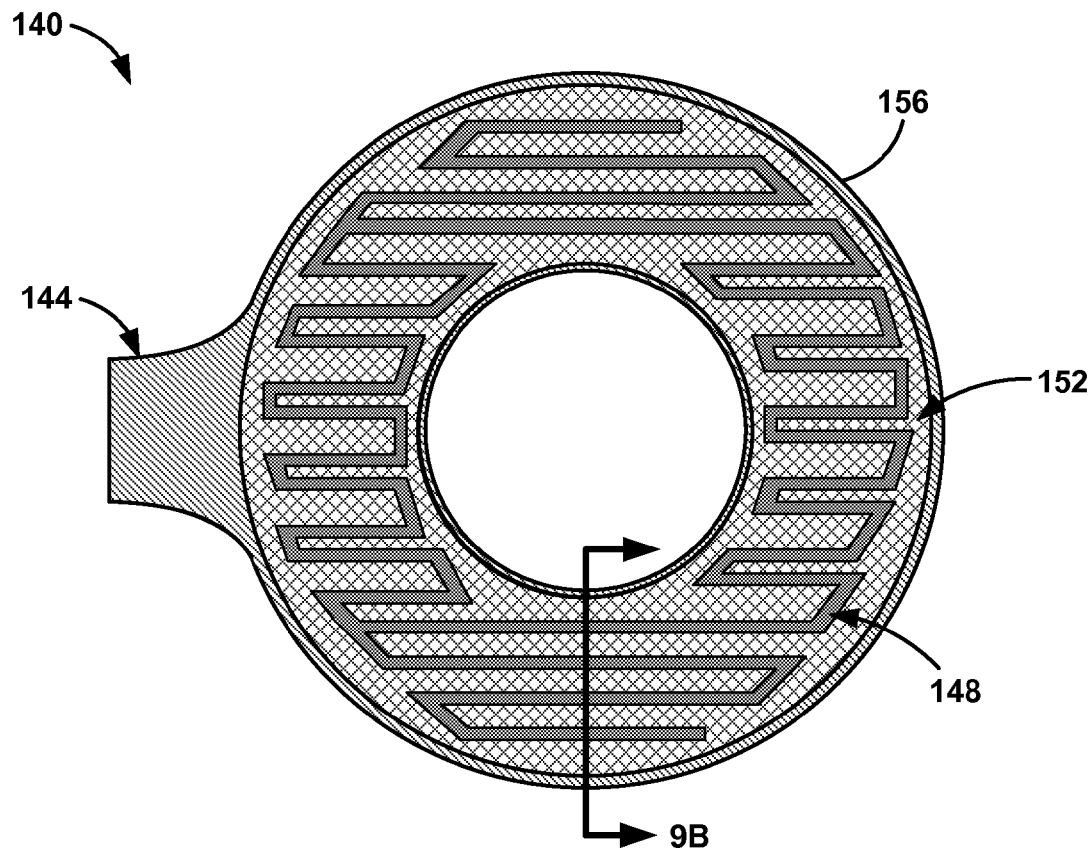
FIGS. 9A and 9B are cross-sectional side views of a phase change material disposed in a lateral zigzag pattern in conjunction with an energy transfer coil.
Figure 9B:
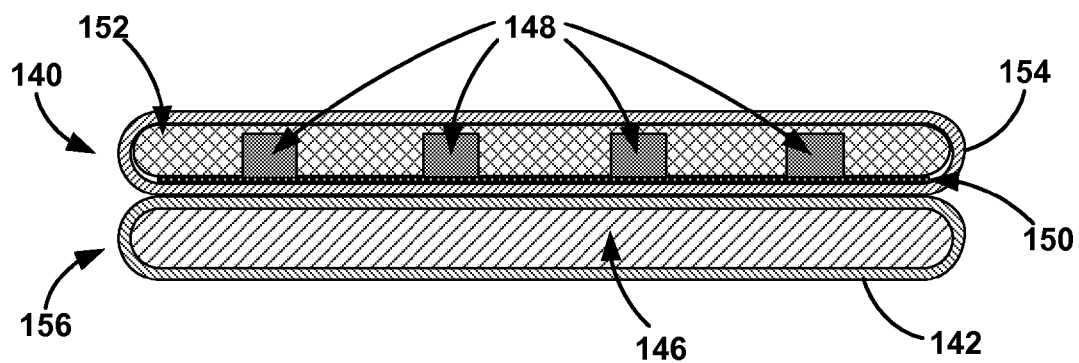

FIGS. 9A and 9B are cross-sectional side views of a phase change material disposed in lateral zigzag pattern 148 in conjunction with energy transfer coil 156. Heat sink device 140 is an example of heat sink device 28 of FIG. 1, and energy transfer coil 156 is an example of energy transfer coil 26 of FIG. 1. As shown in FIG. 9A, heat sink device 140 includes phase change material in lateral zigzag pattern 148. Energy transfer coil 156 includes connector portion 144 for coupling coil 146 with a charging device. FIG. 9A shows heat sink device 140 with the top of housing 154 removed to expose lateral zigzag pattern 148 on top of, or adjacent to, energy transfer coil 156. Wire coil 146 is shown as a solid component in FIG. 9B for ease of illustration, but coil 146 may be an in-plane spiral of wire similar to that of energy transfer coil 26 of FIG. 2A.

Heat sink device 140 includes phase change material disposed in lateral zigzag pattern 148 adjacent to energy transfer coil 156. Lateral zigzag pattern 148 may be similar to radial zigzag pattern 128 of FIG. 8A, but lateral zigzag pattern 148 traverses the interior surface of heat sink device 140 from one side edge of heat sink device 140 to the other side. This configuration of lateral zigzag pattern 148 may be configured to promote curvature of heat sink device 140 and energy transfer coil 156 in predetermined directions when heat sink device 140 and energy transfer coil 156 are removably attached. For example, lateral zigzag pattern 148 may promote flexibility or curvature of heat sink device 140 in a single direction across the heat sink device 140. In other words, lateral zigzag pattern 148 may promote curling of heat sink device 140 from the endpoints of lateral zigzag pattern 148 toward the middle of heat sink device 140. In other examples, lateral zigzag pattern 148 may be oriented in any direction within housing 154 of heat sink device 140. Lateral zigzag pattern 148 may include any number of sections to cover less or more area of heat sink device 140 with phase change material. Lateral zigzag pattern 148 may be disposed on one side of energy transfer coil 156 or on both opposing sides of energy transfer coil 156 in other examples.

FIG. 9B is an illustration of a cross-section of heat sink device 140 indicated by section 9B in FIG. 9A. Heat sink device 140 is shown with the phase change material of lateral zigzag pattern 148 within housing 154. The thickness of heat sink device 140 may be less than, equal to, or greater than the thickness of energy transfer coil 156. Housing 154 may thus encase the phase change material of lateral zigzag pattern 148 and housing 142 may this encase wire coil 146 of energy transfer coil 156.

Similar to radial zigzag pattern 128 of FIG. 8B, lateral zigzag pattern 148 may be formed by channels within containment structure 152. Film 150 may be provided to seal the phase change material within the channels of containment structure 152. Containment structure 152 may be constructed of a thermally conductive or thermally insulative material that is also flexible. Film 150 may be applied to the surface of containment structure 152 to retain the phase change material within the channels of containment structure 152. Film 130 may be adhered to containment structure 152 with an adhesive or other bonding technique. Film 150 may also be configured to contact housing 154 and transfer heat to the phase change material in lateral zigzag pattern 148 from energy transfer coil 156 when attached. Alternatively, containment structure 152 may include two mating portions that are filled with the phase change material and, when combined, contain the phase change material in the channels of the two mating portions.

Similar to energy transfer device 34 of FIG. 3B, heat sink device 140 may alternatively include one or more flexible tubes, beads, or a woven material to contain the phase change material in lateral zigzag pattern 148 at predetermined locations within housing 154. In other examples, lateral zigzag pattern 148 may be formed in one or more channels or cavities of housing 154.

Figure 10A:
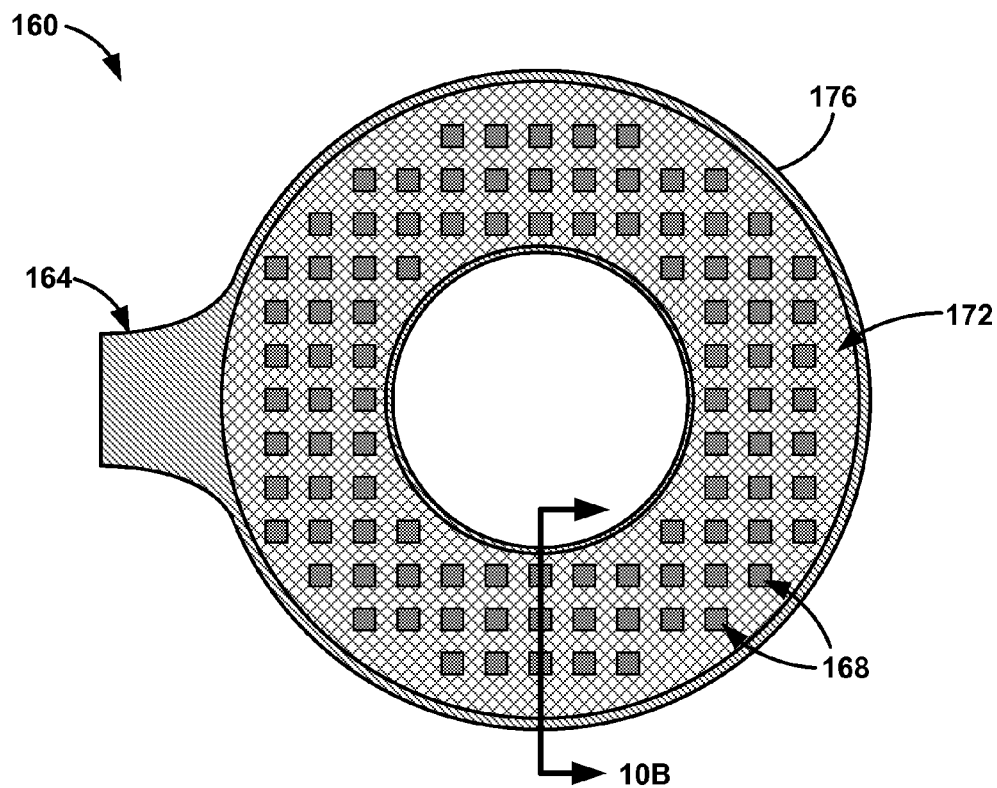
FIGS. 10A and 10B are cross-sectional side views of a phase change material disposed in a plurality of self-contained volumes distributed in conjunction with an energy transfer coil.
Figure 10B:
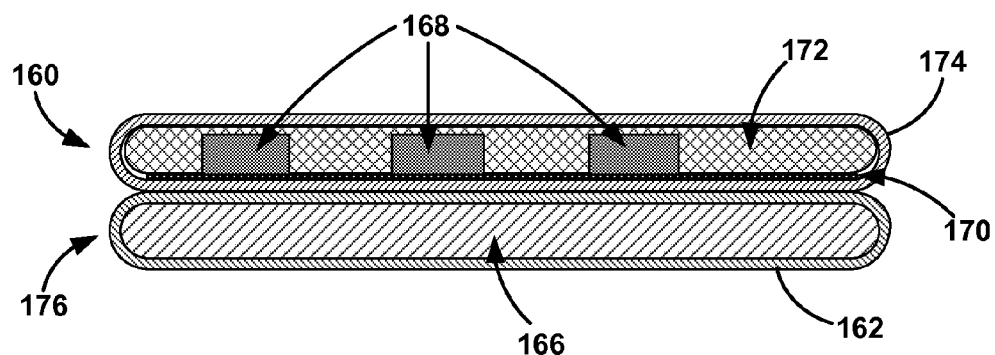

FIGS. 10A and 10B are cross-sectional side views of a phase change material disposed in a plurality of self-contained volumes 168 distributed in conjunction with energy transfer coil 176. Heat sink device 160 is an example of heat sink device 28 of FIG. 1, and energy transfer coil 176 is an example of energy transfer coil 26 of FIG. 1. In addition, heat sink device 160 may be very similar to heat sink device 140 of FIGS. 9A and 9B. However, heat sink device 160 may include a plurality of self-contained volumes 168 instead of a continuous zigzag pattern. Heat sink device 160 includes phase change material in self-contained volumes 168. Energy transfer coil 176 may include wire coil 166, housing 162, and connector portion 164. The phase change material of self-contained volumes 168 may be provided within housing 174 (not shown in FIG. 10A). Volumes 168 may, in effect, form multiple, discrete islands of phase change material distributed across the area of heat sink device 160.

Self-contained volumes 168 may be any depression, cavity, or encapsulated volume that contains phase change material. For example, self-contained volumes 168 may be a plurality of individual beads or capsules. Each of the beads or capsules may include phase change material encapsulated with a thermally conductive material, such as an inert and chemically stable polymer. Many small volumes of phase change material may prevent phase change material from pooling or migrating when the phase change material is heated to the liquid state. Many self-contained volumes 168 may also promote flexibility of heat sink device 160. Heat sink device 160 may include any number of self-contained volumes 168. In general, heat sink device 160 may include as few as two self-contained volumes or more than one hundred self-contained volumes. Self-contained volumes 168 may be distributed in a grid, concentric circles, a random pattern, or any other pattern selected to perform the functions described herein.

FIG. 10B is an illustration of a cross-section of heat sink device 160 and energy transfer coil 176 indicated by section 10B in FIG. 10A. Heat sink device 160 is shown with the phase change material of self-contained volumes 168 within housing 174 and energy transfer coil 176 is shown with wire coil 166 within housing 162. Housing 174 and 162 may be constructed of a flexible material that reduces any inhibition of flexibility of coil 166 and/or self-contained volumes 168 when heat sink device 160 is removably attached to energy transfer coil 176.

Self-contained volumes 168 may be formed as cavities or depressions within containment structure 172. Film 170 may be provided to seal the phase change material within the cavities of containment structure 172. Containment structure 172 may be constructed of a thermally conductive or thermally insulative material that is also flexible. Film 170 may be applied to the surface of containment structure 172 to retain the phase change material within the cavities of containment structure 172. Film 150 may be adhered to containment structure 152 with an adhesive or other bonding technique. Film 170 may also be configured to contact the interior of housing 174 to transfer heat from energy transfer coil 176 to the phase change material in self-contained volumes 168. Alternatively, containment structure 172 may include two mating portions that are filled with the phase change material and, when combined, contain the phase change material in the channels of the two mating portions. Self-contained volumes 168 may be shaped as spheres, cubes, domes, or any other shapes.

Similar to heat sink device 34 of FIG. 3B, heat sink device 160 may alternatively include one or more flexible tubes, beads, or a woven material to contain the phase change material in self-contained volumes 168 at predetermined locations within housing 174. In other examples, self-contained volumes 168 may be formed in one or more cavities or depressions of housing 174. Alternatively, self-contained volumes 168 may each be a bead or other encapsulation structure that retains the phase change material.

Figure 11A:
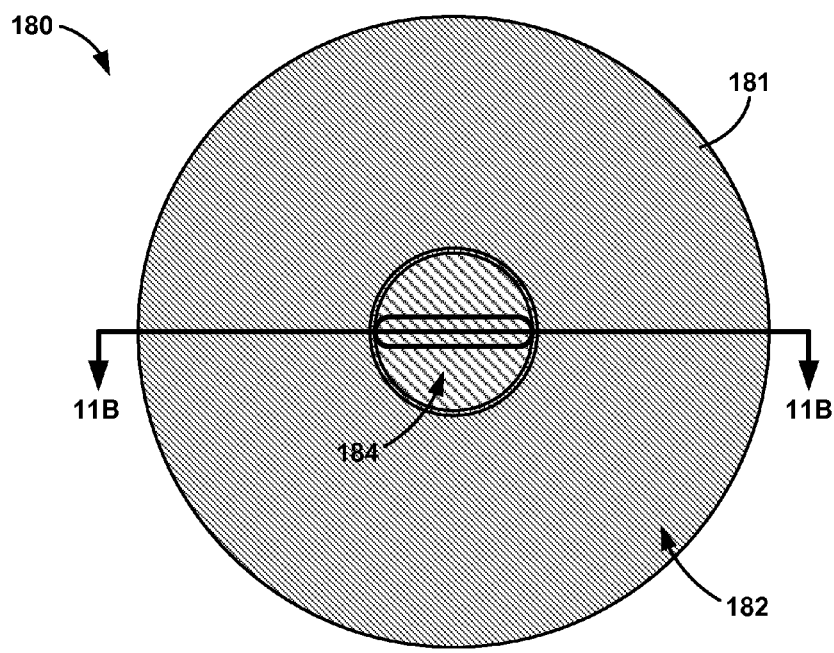
FIGS. 11A and 11B include a top view and a cross-sectional side view of a heat sink device removably attached to an energy transfer coil with a threaded member.
Figure 11B:
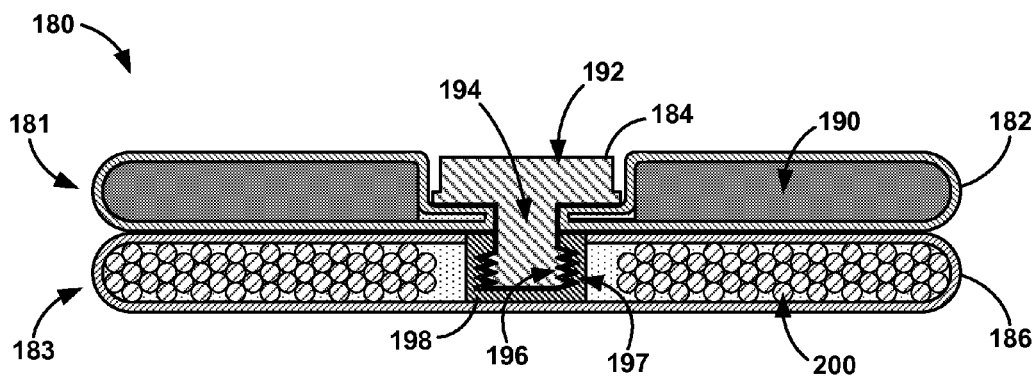

FIGS. 11A and 11B include a top view and a cross-sectional side view of system 180 that includes heat sink device 181 removably attached to energy transfer coil 183 with threaded member 184. Heat sink device 180 is an example of heat sink device 28 of FIG. 1, and energy transfer coil 183 is an example of energy transfer coil 26 of FIG. 1. As shown in FIG. 11A, heat sink device 181 includes a disk-shaped housing 182 with threaded member 184 disposed at the center of housing 182. Heat sink device 181 may be removably attached to an energy transfer coil to manage the temperature of the energy transfer coil during a recharge session. Threaded member 184 may be at least a portion of the coupling mechanism used to attach heat sink device 181 to energy transfer coil 183.

Heat sink device 181 is shown as a disc or circular shaped structure. However, heat sink device 181 may be configured into any shape appropriate for absorbing heat from energy transfer coil 183. In other examples, heat sink device 181 may have an oval, triangular, square, rectangular, or amorphous shape. The shape of heat sink device 181 may be selected to increase the contact area between heat sink device 181 and energy transfer coil 183.

FIG. 11B is an illustration of a cross-section of heat sink device 181 and energy transfer coil 183 indicated by section 11B in FIG. 11A. Together, heat sink device 181 and energy transfer coil 183 may be considered system 180. Energy transfer coil 183 may include wire coil 200, housing 186, and retaining block 198 that includes threaded surface 197. Wire coil 200 may include second windings of a coil. The windings may be within a plane (e.g., an in-plane spiral of wire). Wire coil 200 may include one or more layers of coil windings. The number of windings in wire coil 200 may be selected based on the energy to be transferred when charging IMD 14, the thickness of the wire, and the flexibility desired for a particular application.

Housing 186 may contain wire coil 200. In some examples, housing 186 may be constructed of a flexible material that conforms to non-planar skin surfaces. Housing 186 may also be thermally conductive such that heat generated within wire coil 200 can be transmitted to phase change material 190. In addition, housing 186 may include or be attached to retaining block 198. Retaining block 198 may be disposed within the center of housing 186 and provide a receptacle for threaded member 184. Specifically, retaining block 198 may include threaded surface 197 configured to mate with threaded structure 196 of threaded member 184. In this manner, both retaining block 198 and threaded member 184 may be portions of a coupling mechanism configured to retain at least a portion of housing 182 in thermal communication with a surface of housing 186 of energy transfer coil 183. In other examples, threaded surface 197 may be formed directly in housing 186.

Heat sink device 181 may include phase change material 190, housing 182, and threaded member 184 (e.g., a coupling mechanism). Housing 182 may be shaped to contain phase change material 190 within the interior volume (e.g., a disk-shaped volume similar to disk-shaped volume 88 of heat sink device 80 in FIGS. 6A, 6B, and 6C) of housing 182. Housing 182 may also be constructed of a flexible material that deforms to the surface of energy transfer coil 183 and/or the skin surface of patient 14.

Housing 182 may also be shaped to include threaded member 184. Housing 182 may form a center hole configured to accept threaded member 184. Threaded member 184 may include knob 192, shaft 194, and threaded structure 196. A user may apply pressure to either side of knob 192 and exert a torque about threaded member 184 to unscrew or screw threaded structure 196 against threaded surface 197. The torque applied to knob 192 may be transmitted down shaft 194 and to threaded structure 196 to attach or remove heat sink device 181 from energy transfer coil 183. In other examples, threaded member 184 may be a separate component that is merely provided as part of system 180 to removably attach heat sink device 180 to energy transfer coil 183.

In this manner, threaded member 184 may be used to removably attach heat sink device 181 to energy transfer device 183. When attached, housing 182 may be in thermal communication with energy transfer coil 183 when housing 182 is in contact with at least a portion of the surface of energy transfer coil 183. In some examples, system 180 may include one or more coupling mechanisms located at various positions with respect to heat sink device 181 and energy transfer coil 183. Multiple coupling mechanisms may be desirable to retain housings 182 and 186 in contact with each other when energy transfer coil 186 and heat sink device 181 are both flexible.

The coupling mechanism that retains heat sink 181 and energy transfer coil 183 in thermal communication may vary in other examples. For example, the threaded structure of heat sink device 181 may be formed by housing 182. Housing 182 may include an extruded threaded structure similar to that of threaded member 184. Alternatively, housing 182 may form a threaded surface in a depression that accepts a threaded structure formed of or attached to housing 186 of energy transfer coil 183. Alternatively, housing 182 may form a threaded structure or a series of tabs along the outer circumference of the housing. The outer circumference threaded structure may be configured to mate with a threaded surface of housing 186 along the outer surface of energy transfer coil 26. In this case, heat sink device 181 may be rotated with respect to energy transfer coil 183 to engage the circumferential threaded structure with the circumferential threaded surface such that heat sink device 181 is removably attached to energy transfer coil 26. These circumferential threaded structures and surfaces may resemble, for example, a lid (e.g., heat sink device 181) that screws onto a jar (e.g., energy transfer coil 183). In some examples, the coupling mechanism may include threaded surfaces and associated structures of housings 182 and 186 at multiple different radial positions. It is noted that any coupling mechanisms described herein may be formed from a housing, attached to a housing, or otherwise configured to couple to a housing.

Figure 12A:
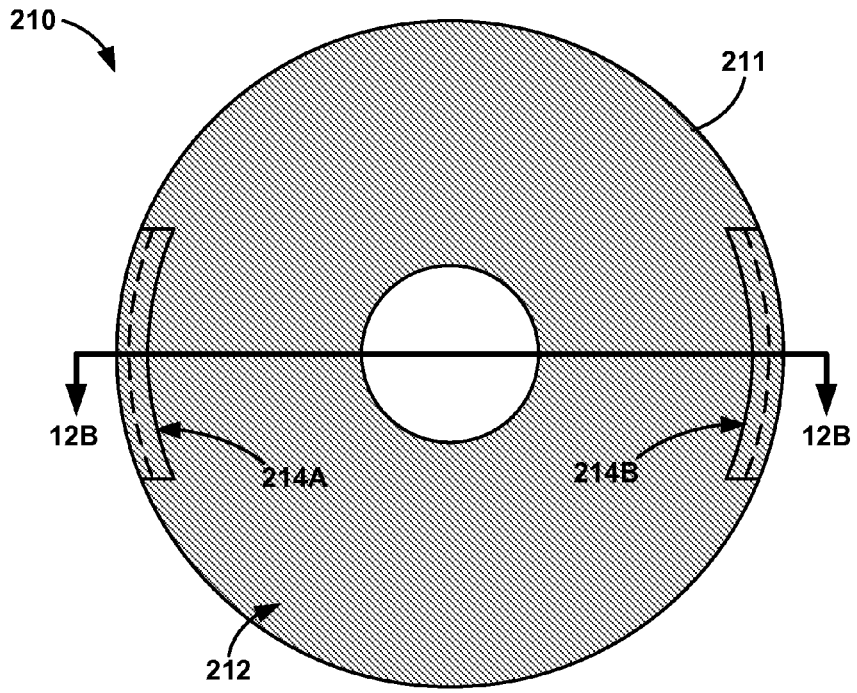
FIGS. 12A and 12B include a top view and a cross-sectional side view of a heat sink device removably attached to an energy transfer coil with two retaining members.
Figure 12B:
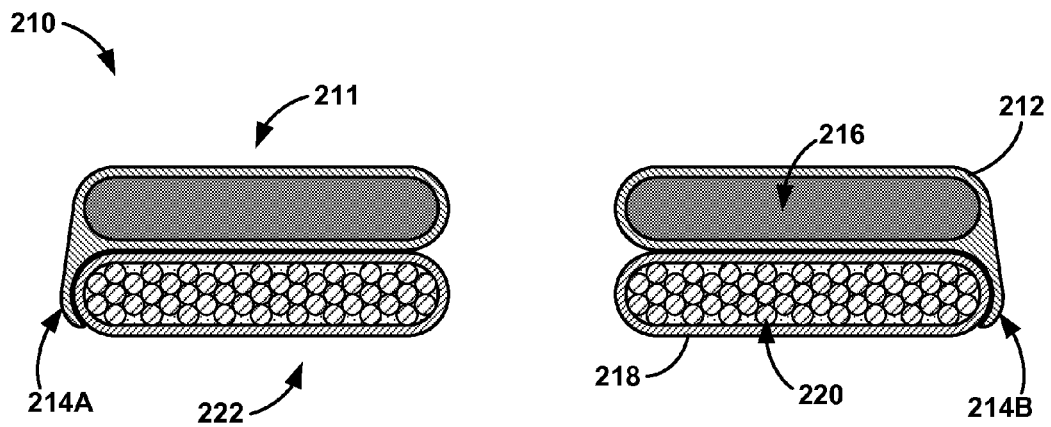

FIGS. 12A and 12B include a top view and a cross-sectional side view of heat sink device 211 removably attached to energy transfer coil 222 with two retaining members 214A and 214B. Heat sink device 211 is an example of heat sink device 28 of FIG. 1, and energy transfer coil 222 is an example of energy transfer coil 26 of FIG. 1. As shown in FIG. 12A, heat sink device 211 includes a disk-shaped housing 212 with retaining members 214A and 214B (collectively "retaining members 214"). Heat sink device 211 may be removably attached to energy transfer coil 222 to manage the temperature of the energy transfer coil during a recharge session.

Each of retaining members 214 may be arms that extend away from the surface of housing 212 and are shaped to retain energy transfer coil 222 between retaining members 214 and housing 212. Retaining members 214 may include a curved length that corresponds to the circumference of housing 212 and/or the circumference of energy transfer coil 222. In addition, retaining members 214 may include a lip indicated by the dotted lines that ends radially inward at the end of each retaining member. Retaining members 214 may be at least a portion of the coupling mechanism used to attach heat sink device 211 to energy transfer coil 222.

Heat sink device 211 is shown as a disc or circular shaped structure. However, heat sink device 211 may be configured into any shape appropriate for absorbing heat from energy transfer coil 222. In other examples, heat sink device 211 may have an oval, triangular, square, rectangular, or amorphous shape. The shape of heat sink device 211 may be selected to increase the contact area between heat sink device 222 and energy transfer coil 222. In this manner, any heat sink devices described herein may be configured with dimensions and/or a shape selected to absorb heat from one or more energy transfer coils.

FIG. 12B is an illustration of a cross-section of heat sink device 211 and energy transfer coil 222 indicated by section 12B in FIG. 12A. Together, heat sink device 211 and energy transfer coil 222 may be considered as system 210. Energy transfer coil 222 may include wire coil 222 and housing 218. Wire coil 220 may be substantially similar to wire coil 200 of FIG. 11B. Housing 218 of energy transfer coil 222 may contain wire coil 220. In some examples, housing 218 may be constructed of a flexible material that conforms to non-planar skin surfaces. Housing 218 may also be thermally conductive such that heat generated within wire coil 220 can be transmitted to phase change material 216.

Heat sink device 211 may include phase change material 216, housing 212, and retaining members 214 (e.g., a coupling mechanism). Housing 212 may be shaped to contain phase change material 216 within the interior volume (e.g., a disk-shaped volume similar to disk-shaped volume 88 of heat sink device 80 in FIGS. 6A, 6B, and 6C) of housing 212. Housing 212 may also be constructed of a flexible material that deforms to the surface of energy transfer coil 222 and/or the skin surface of patient 14.

Retaining members 214 may be constructed as curved arms configured to match the curvature of the outside of housing 218. In other examples, retaining members 214 may extend completely around the edge of housing 218 or housing 218 may include three or more retaining members 214 positioned equidistant around the edge of housing 218 or at varying circumferential positions. In some examples, retaining members 214 may be shaped with angular bends instead of the curvature shown in FIG. 12B. For example each of retaining members 214 may be shaped like an "L". In any example, retaining members 214 may be constructed of a material that deforms radially outward such that each retaining member 214 "snaps" into place around the edges of housing 218. In this manner, retaining member 214 may provide elastic deformation that allows radial changing positions, e.g., at least some degree of flexibility, to accept housing 218. In some examples, retaining members 214 may be biased to form a diameter between the retaining members that is smaller than the diameter of housing 218. This bias may then provide a force against housing 218 such that energy transfer coil 22 is retained between retaining members 214 and against heat sink device 211. Although retaining members 214 may be formed of housing 212, retaining members 214 may be separate elements attached to housing 212 in other examples.

In this manner, retaining members 214 may be used to removably attach heat sink device 211 to energy transfer coil 222. When attached, housing 211 may be in thermal communication with energy transfer coil 222 when housing 211 is in contact with at least a portion of the surface of energy transfer coil 222. In some examples, heat sink device 211 may include three or more retaining members in other examples. Multiple coupling mechanisms may be desirable to retain housings 211 and 222 in contact with each other when energy transfer coil 222 and heat sink device 211 are both flexible.

Figure 13A:
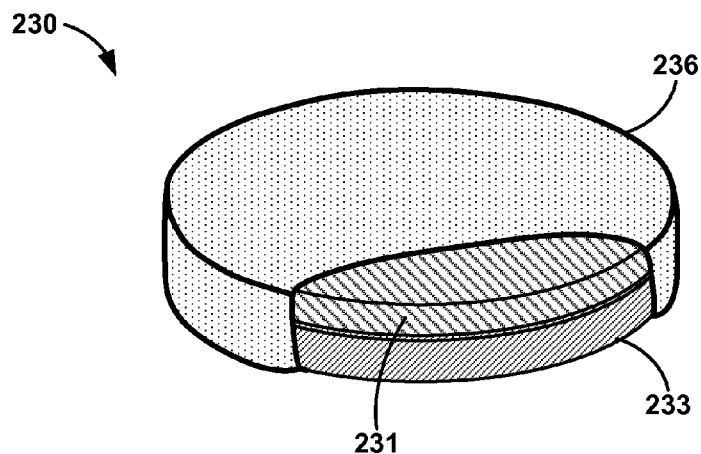
FIGS. 13A and 13B include a perspective view and a cross-sectional side view of a heat sink device removably attached to an energy transfer coil with an elastic sheath.
Figure 13B:
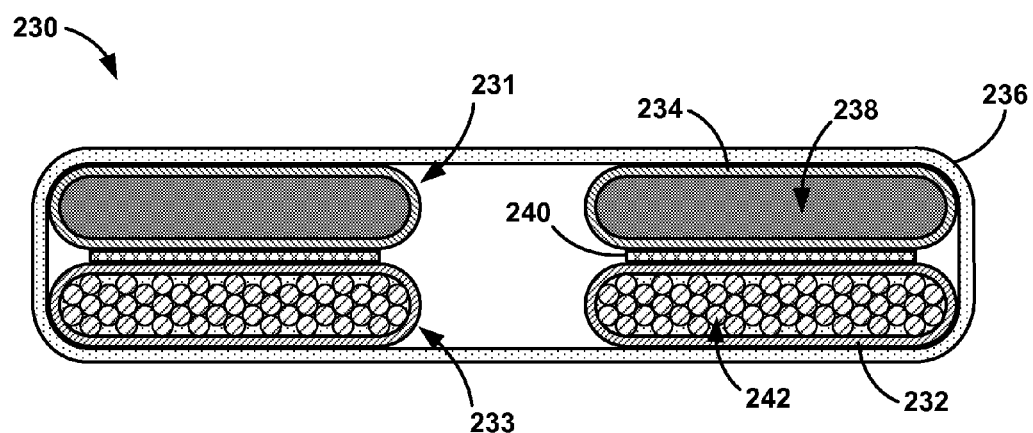

FIGS. 13A and 13B include a perspective view and a cross-sectional side view of heat sink device 231 removably attached to energy transfer coil 233 with elastic sheath 236. Heat sink device 231 is an example of heat sink device 28 of FIG. 1, and energy transfer coil 233 is an example of energy transfer coil 26 of FIG. 1. As shown in FIG. 13A, heat sink device 231 includes a disk-shaped housing 234. Heat sink device 231 may be removably attached to energy transfer coil 233 with elastic sheath 236 to manage the temperature of energy transfer coil 233 during a recharge session.

Elastic sheath 236 may be formed as a pouch or pocket configured to enclose at least a portion of both heat sink device 231 and energy transfer coil 233 and function as a coupling mechanism. Although both heat sink device 231 and energy transfer coil 233 may be removed from the elastic sheath, either heat sink device 231 or energy transfer coil 233 may be formed within, e.g., permanently within, the elastic sheath in other examples. The opening in elastic sheath 236 may be formed along the circumferential edge of the sheath such that each of heat sink device 231 may be slide sideways into the sheath. Alternatively, elastic sheath 236 may include an opening on the bottom or top of elastic sheath 236 such that each of heat sink device 231 and energy transfer coil 233 may be placed into elastic sheath 236 one at a time in a stacking configuration. Elastic sheath 236 may also provide a hole or other access panel that allows a wire or cable to exit the elastic sheath. Elastic sheath 236 may be constructed of an elastic woven material, an elastic polymer, or other material capable of elastic deformation. Heat sink device 231 is shown as a disc or circular shaped structure. However, heat sink device 231 may be configured similar to heat sink device 211 of FIGS. 12A and 12B into any shape appropriate for absorbing heat from energy transfer coil 233.

FIG. 13B is an illustration of a cross-section of heat sink device 231 and energy transfer coil 233 indicated by section 13B in FIG. 13A. Together, heat sink device 231 and energy transfer coil 233 may be considered as system 230. Energy transfer coil 233 may include wire coil 242 and housing 232. Wire coil 242 may be substantially similar to wire coil 200 of FIG. 11B. Housing 232 of energy transfer coil 233 may contain wire coil 242. In some examples, housing 232 may be constructed of a flexible material that conforms to non-planar skin surfaces. Housing 232 may also be thermally conductive such that heat generated within wire coil 242 can be transmitted to phase change material 238.

Heat sink device 231 may include phase change material 238 and housing 234. Housing 234 may be shaped to contain phase change material 238 within the interior volume (e.g., a disk-shaped volume similar to disk-shaped volume 88 of heat sink device 80 in FIGS. 6A, 6B, and 6C) of housing 234. Housing 234 may also be constructed of a flexible material that deforms to the surface of energy transfer coil 233 and/or the skin surface of patient 14. Elastic sheath 236 may thus be used by the user to removably attach heat sink device 231 to energy transfer coil 233. Elastic sheath 236 may undergo elastic deformation sufficient to add and remove at least one of heat sink device 231 and energy transfer coil 233.

In addition, thermally conductive material 240 may be provided to facilitate heat transfer between energy transfer coil 233 and heat sink device 231. Thermally conductive material 240 may have a thickness that is at least partially deformable to increase the surface area contact between housings 234 and 232. Thermally conductive material 240 may be constructed of a polymer, composite, adhesive, or any other material that facilitates the transfer of heat. Although thermally conductive material 240 may be a separate element in system 230, thermally conductive material 240 may be attached to or otherwise a part of either housing 234 or housing 232. In other examples, heat sink device 231 may be thermally coupled to energy transfer device 233 without thermally conductive material 240.

In other examples, elastic sheath 236 may be replaced with an alternative device that connects heat sink device 231 and energy transfer coil 233. For example, system 230 may utilize a strap, button tabs, a fabric pouch, adhesive tape, or any other structure that wraps at least partially around heat sink device 231 and energy transfer coil 233. In alternative examples, heat sink device 231 and energy transfer coil 233 may be coupled with a coupling mechanism that includes a hook and loop closure device (e.g., hooks may be disposed on a surface of heat sink device 231 and loops may be disposed on a surface of energy transfer coil 231).

Figure 14A:
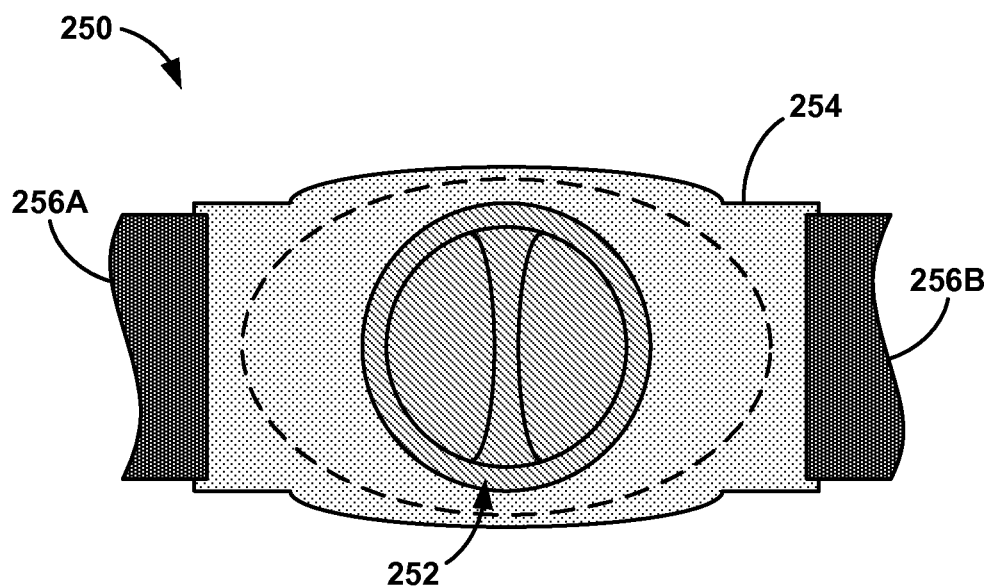
FIGS. 14A and 14B include a top view and a side view of a heat sink device removably attached to an energy transfer coil in conjunction with skin of a patient.
Figure 14B:
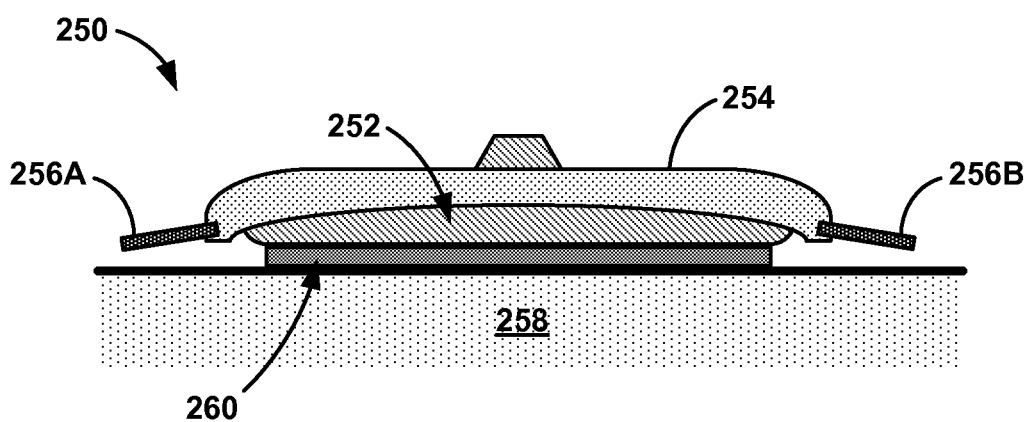

FIGS. 14A and 14B include a top view and a side view of a heat sink device 260 removably attached to energy transfer coil 252 in conjunction with skin 258 of patient 14. Heat sink device 260 is an example of heat sink device 28 of FIG. 1, and energy transfer coil 252 is an example of energy transfer coil 26 of FIG. 1. As shown in FIG. 14A, system 250 includes energy transfer coil 252 retained within clip 254. Energy transfer coil 252 may include an oval shaped housing that includes a coil of wire used to wirelessly transfer energy. Clip 254 may be configured such that energy transfer coil 252 fits within clip 254 for attachment to patient 14. Clip 254 is then retained against patient 14 with belt 256. Belt ends 256A and 256B couple to clip 254 and are a part of belt 256 that wraps around portion of the body of patient 14. In this manner, clip 254 and belt 256 may be a coupling mechanism.

As shown in FIG. 14B, system 250 also includes heat sink device 260 removably attached to energy transfer coil 252 between energy transfer coil 252 and skin 258. Heat sink device 260 may be attached to energy transfer coil 260 by the pressure from energy transfer coil 252 against skin 258. In other words, belt 256 may retain clip 254 and energy transfer coil 252 against skin 258. Then heat sink device 260 may be positioned between energy transfer coil 252 and skin 258. In other examples, heat sink device 260 may be positioned between clip 254 and energy transfer coil 252. In any case, heat sink device 260 may include phase change material that absorbs heat from energy transfer coil 252 when the housing of heat sink device 260 is in contact (e.g., thermal communication) with energy transfer coil 252.

Heat sink device 260 may include phase change material configured similar to any phase change material of various heat sink devices 260 described herein. Heat sink device 260 may be shaped as a circular disk, oval disk, rectangular pad, or any other shape that may or may not be matched with the shape of energy transfer coil 252. In addition, heat sink device 260 may be attached energy transfer coil 252 with an adhesive or a tacky surface of a polymer housing of heat sink device 260. The housing and phase change material of heat sink device 260 may also be configured to be flexible such that heat sink device 260 may conform to skin 258 and/or energy transfer coil 252.

Figure 15A:
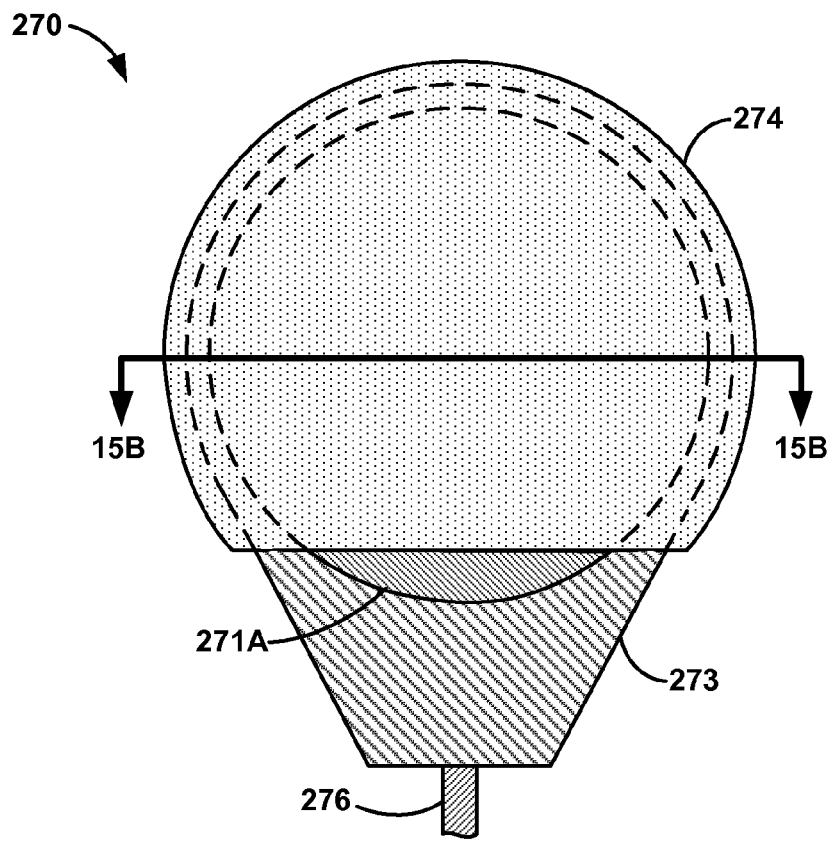
FIGS. 15A and 15B include a top view and a cross-sectional side view of a heat sink device removably attached to an energy transfer coil with an elastic sheath.
Figure 15B:
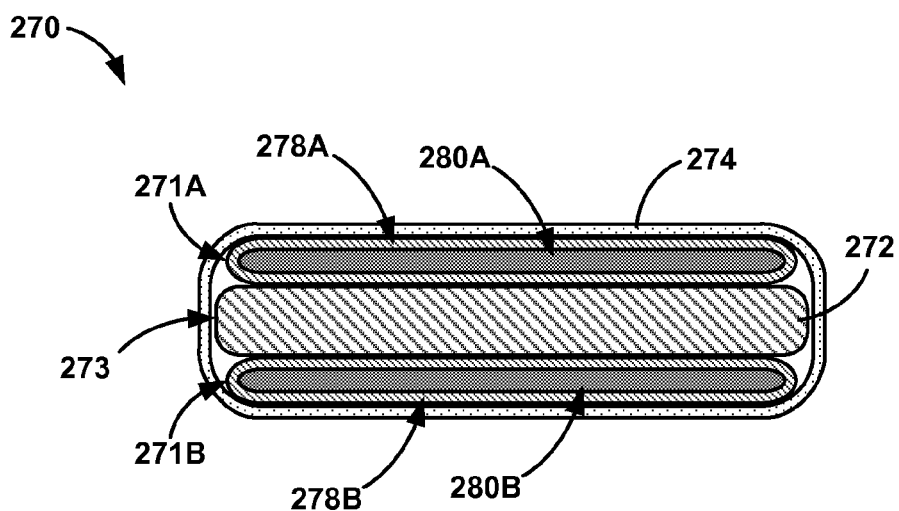

FIGS. 15A and 15B include a top view and a cross-sectional side view of heat sink devices 271A and 271B removably attached to energy transfer coil 273 with elastic sheath 274. Heat sink devices 271A and 271B (collectively "heat sink devices 271") are examples of heat sink device 28 of FIG. 1, and energy transfer coil 273 is an example of energy transfer coil 26 of FIG. 1. More specifically, heat sink devices 271 may be substantially similar to heat sink device 231 of FIGS. 13A and 13B. In addition, elastic sheath 274 may be substantially similar to elastic sheath 236 of FIGS. 13A and 13B.

As shown in FIG. 15A, heat sink device 271A is a disk-shaped device configured to mate against energy transfer coil 273. With the aid of elastic sheath 274 (e.g., a coupling mechanism), heat sink device 271A may be removably attached to energy transfer coil 273. Since elastic sheath 236 may force heat sink device 271A into thermal communication with energy transfer coil 273, heat sink device 271A may manage the temperature of energy transfer coil 273 during a recharge session.

Elastic sheath 274 may be formed as a pouch or pocket configured to enclose at least a portion of both heat sink devices 271 and energy transfer coil 273 and function as a coupling mechanism. Both heat sink devices 271 and energy transfer coil 273 may be removed from elastic sheath 274. Although heat sink devices 271 and energy transfer coil 273 may be designed and configured to mate with each other, heat sink devices 271 and elastic sheath 274 may be constructed as an aftermarket system to manage the temperature of previously manufactured energy transfer coil 273. In this manner, heat sink devices 271 and elastic sheath 274 may be used with a variety of different energy transfer coils for different applications and from different manufacturers. Other heat sink devices described herein may also be retroactively applied to energy transfer coils not originally configured to mate with a heat sink device.

FIG. 15B is an illustration of a cross-section of heat sink devices 271 and energy transfer coil 273 indicated by section 15B in FIG. 15A. Heat sink devices 271 may be positioned on opposing sides of energy transfer coil 273. In addition, elastic sheath 274 is shown as surrounding heat sink devices 271 and energy transfer coil 273. Together, heat sink devices 271, energy transfer coil 273, and elastic sheath 274 may be considered as system 270. Energy transfer coil 273 may include a wire coil (not shown) within housing 272. Housing 272 may also be thermally conductive such that heat generated during the recharge session can be transmitted to phase change material 280A and 280B.

Heat sink devices 271 may include phase change material 280A and 280B within respective housings 278A and 278B. Similar to other heat sink devices described herein, phase change material 280A and 280B may be contained within flexible tubes, beads, channels, or larger volumes. Housings 278A and 278B may also be constructed of a flexible material that deforms to the surface of energy transfer coil 273 and/or the skin surface of patient 14. Elastic sheath 274 may thus be used by the user to removably attach heat sink devices 271 to energy transfer coil 273. Elastic sheath 274 may undergo elastic deformation sufficient to add and remove at least one of heat sink devices 271 and energy transfer coil 273.

Figure 16A:
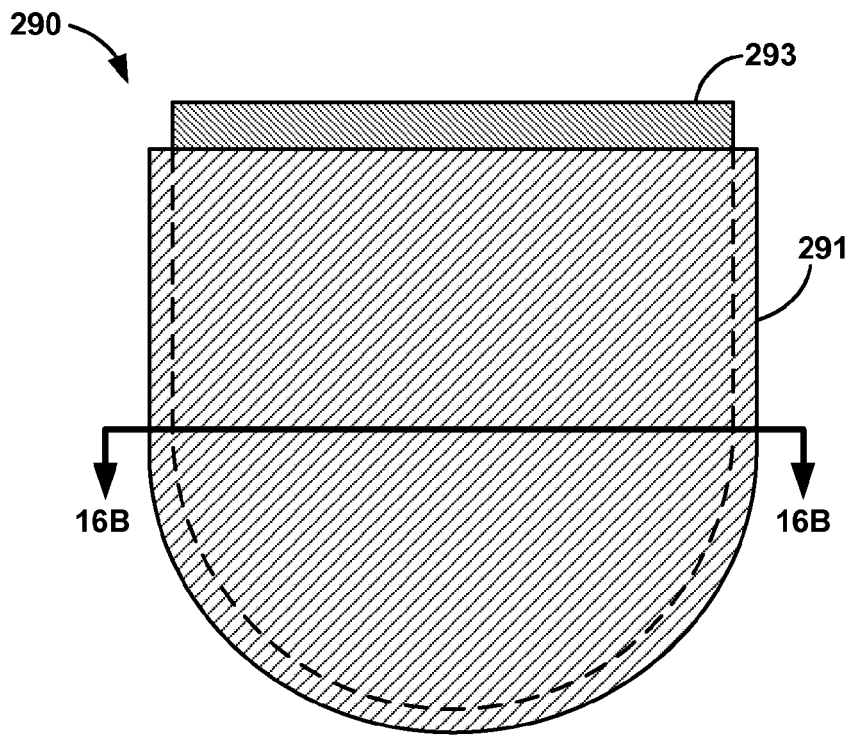
FIGS. 16A and 16B include a top view and a cross-sectional side view of a heat sink device removably attached to an energy transfer coil with a retaining member.
Figure 16B:
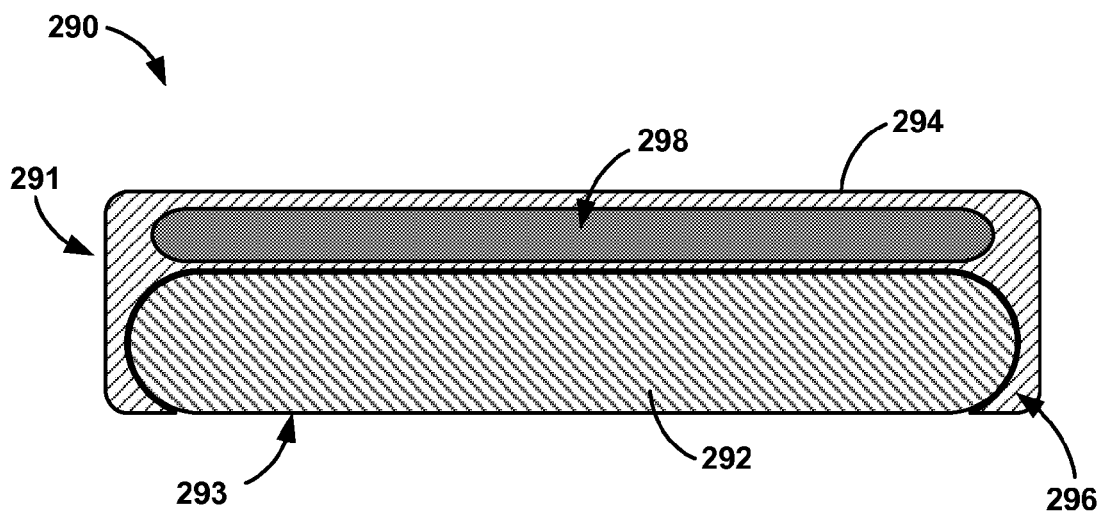

FIGS. 16A and 16B include a top view and a cross-sectional side view of heat sink device 291 removably attached to energy transfer coil 293 with a retaining member. Heat sink device 291 is an example of heat sink device 28 of FIG. 1, and energy transfer coil 273 is an example of energy transfer coil 26 of FIG. 1. As shown in FIG. 16A, heat sink device 281 is a device configured to mate against energy transfer coil 293. Energy transfer coil 293 may be a wireless energy transfer coil. In other words, energy transfer coil 293 may be a self-contained charging device that includes an energy source and a charging circuit to drive electrical current through wire of a primary coil within energy transfer coil 293. Alternatively, energy transfer coil 293 may be tethered to a charging device (e.g., charging device 22 of FIG. 1). Heat sink device 291 may include both a phase change material and a coupling mechanism that retains heat sink device 291 in thermal communication with energy transfer coil 293. Heat sink device 291 may be configured to mate with energy transfer coil 293, but energy transfer coil 293 may not have been designed to be coupled with heat sink device 291. Both heat sink device 291 and energy transfer coil 293 may be shaped as a rectangle with one side being shaped as a half-circle.

FIG. 16B is an illustration of a cross-section of heat sink device 291 and energy transfer coil 293 indicated by section 16B in FIG. 16A. Heat sink device 291 and energy transfer coil 293 may be included within system 290. Energy transfer coil 293 may include a wire coil (not shown) within housing 292. Housing 292 may also be thermally conductive such that heat generated during the recharge session can be transmitted to phase change material 298 of heat sink device 291.

Heat sink device 291 may include phase change material 298 contained within housing 294. Similar to other heat sink devices described herein, phase change material 298 may be contained within flexible tubes, beads, channels, or larger continuous volumes. Housing 294 may also be formed with retaining member 296 that extends away from housing 294. Retaining member 296 may have a curved inner surface configured to mate with the curved outer surface of housing 292 of energy transfer coil 293. In this manner, retaining member 296 may be shaped to at least partially surround housing 292 to removably attach heat sink device 291 to energy transfer coil 293.

Retaining member 296 may be a continuous structure around the perimeter of housing 294. In other examples, retaining member 296 may include two or more segments that are spaced around the circumference of housing 294. As shown in FIG. 16A, energy transfer coil 293 may be slid along housing 294 and between opposing surfaces of retaining member 296 to removably attach heat sink device 291 to energy transfer coil 293. In this manner, retaining member 296 may be constructed of a rigid material or a flexible material. Alternatively, retaining member 296 may be constructed of a flexible material that allows retaining member 296 to flex outward to accept energy transfer coil 293 and "snap" back into position to retain the energy transfer coil in contact with heat sink device 291. Although retaining member 296 may be formed of housing 294, retaining member 296 may be a separate structure attached to housing 294 in other examples. Housing 294 may include one or more alternative retaining members that allows energy transfer coil 293 to be attached to heat sink device 291 at different approach angles than shown in FIGS. 16A and 16B.

As described herein, heat sink devices may be attached to energy transfer devices and then removed when no longer needed. In this manner, a housing of a heat sink device may be removably attached to an energy transfer coil. The energy transfer coil may be configured to recharge a rechargeable power source of an implantable medical device and the housing may contain a phase change material configured to absorb heat from the energy transfer coil.

In one example, removably attaching the housing to the energy transfer coil may include rotating a threaded structure of the heat sink device housing against a threaded surface of the energy transfer coil until the housing is in thermal communication with the energy transfer coil. In another example, removably attaching the housing of the heat sink device to the energy transfer coil may include radially bending at least one retaining member of the housing and disposing the energy transfer coil between the at least one retaining member of the heat sink device and the housing. Such a technique may include snapping the energy transfer coil within the retaining members of the heat sink device. In an alternative example, removably attaching the housing of the heat sink device to the energy transfer coil may include retaining the housing and the energy transfer coil within an elastic sheath such that the housing of the heat sink device is in thermal communication with the energy transfer coil.

According to the techniques and devices described herein, phase change material may be provided in contact with an energy transfer coil to manage the temperature of the coil during a charging session. The phase change material may be disposed within a housing such that heat is conducted to the phase change material. In addition, the phase change material may be configured to be positioned between the skin of a patient and the energy transfer coil, on the opposite side of the energy transfer coil than the skin, or some combination thereof. Further, the phase change material may be retained within predetermined locations within the housing of the heat sink device such that the phase change material does not interfere with or otherwise reduce any flexibility of the energy transfer coil.

Various examples have been described. These and other examples are within the scope of the following claims.

What is claimed is:

1. A device comprising:
   a phase change material configured to absorb heat from an energy transfer coil;
   a first housing configured to contain the phase change material; and
   a coupling mechanism configured to removably attach the first housing to a second housing containing the energy transfer coil.

2. The device of claim 1, wherein the coupling mechanism is configured to retain at least a portion of the first housing in thermal communication with a surface of the second housing containing the energy transfer coil.

3. The device of claim 1, wherein the coupling mechanism comprises a threaded structure configured to mate to a threaded surface of the second housing containing the energy transfer coil.

4. The device of claim 1, wherein the coupling mechanism comprises at least one retaining member that extends away from the first housing and is shaped to retain the second housing containing the energy transfer coil between the at least one retaining member and the first housing.

5. The device of claim 1, wherein the coupling mechanism comprises an elastic sheath configured to retain the first housing in thermal communication with the second housing containing the energy transfer coil.

6. The device of claim 1, wherein the phase change material is disposed in at least one shape configured to conform to at least one of the second housing containing the energy transfer coil and a non-planar skin surface of a patient.

7. The device of claim 1, wherein the first housing comprises one or more channels configured to contain the phase change material.

8. The device of claim 1, further comprising one or more flexible tubes configured to contain the phase change material at predetermined locations within the first housing, wherein the phase change material is disposed within the one or more flexible tubes.

9. The device of claim 8, wherein at least one of the one or more flexible tubes and the first housing is constructed of a thermally conductive elastomer.

10. The device of claim 1, wherein the phase change material is encapsulated in a plurality of beads distributed within the first housing.

11. The device of claim 1, wherein the phase change material comprises a melting point temperature between approximately 35 degrees Celsius and 43 degrees Celsius.

12. The method of claim 1, wherein the energy transfer coil is configured to wirelessly transfer power via inductive coupling.

13. A device comprising:
   means for absorbing heat from an energy transfer coil;
   means for containing the means for absorbing heat; and
   means for removably attaching the containing means to a housing containing the energy transfer coil.

14. The device of claim 13, wherein the means for removably attaching the containing means to the housing containing the energy transfer coil comprises a threaded structure configured to mate to a threaded surface of the housing containing the energy transfer coil.

15. The device of claim 13, wherein the means for removably attaching the containing means to the energy transfer coil comprises at least one retaining member that extends away from the containing means and is shaped to retain the housing containing the energy transfer coil between the at least one retaining member and the containing means.

16. The device of claim 13, wherein the means for removably attaching the containing means to the housing containing the energy transfer coil comprises an elastic sheath configured to retain the containing means in thermal communication with the housing containing the energy transfer coil.

17. The device of claim 13, wherein the means for absorbing heat from an energy transfer coil comprises means for conforming the absorbing means to at least one of the housing containing the energy transfer coil and a non-planar skin surface of a patient.

18. The device of claim 13, wherein the phase change material comprises a melting point temperature between approximately 35 degrees Celsius and 43 degrees Celsius.

19. A system comprising:
   an energy transfer coil configured to recharge a rechargeable power source of an implantable medical device;
   a first housing containing the energy transfer coil; and
   a second housing containing a phase change material and configured to be removably attached to the first housing containing the energy transfer coil, wherein the phase change material is configured to absorb heat from the energy transfer coil.

20. The system of claim 19, wherein the second housing is in thermal communication with the energy transfer coil when the second housing is in thermal communication with a surface of the first housing containing the energy transfer coil.

21. The system of claim 19, wherein the first housing containing the energy transfer coil comprises a threaded surface, and wherein the second housing comprises a threaded structure configured to mate to the threaded surface of the first housing containing the energy transfer coil.

22. The system of claim 19, wherein the second housing comprises at least one retaining member that extends away from the second housing and is shaped to retain the first housing containing the energy transfer coil between the at least one retaining member and the second housing.

23. The system of claim 19, further comprising an elastic sheath configured to retain the second housing in thermal communication with the first housing containing the energy transfer coil.

24. The system of claim 19, wherein the phase change material is disposed in at least one shape configured to conform to at least one of the first housing containing the energy transfer coil and a non-planar skin surface of a patient.

25. The system of claim 19, further comprising a thermally conductive material configured to be disposed between the second housing and the first housing containing the energy transfer coil, wherein the thermally conductive material is deformable to a surface of the first housing containing the energy transfer coil and a surface of the second housing.

26. The system of claim 19, wherein the phase change material comprises a melting point temperature between approximately 35 degrees Celsius and 43 degrees Celsius.

27. The system of claim 19, further comprising an implantable medical device comprising the rechargeable power source and a secondary coil, wherein the secondary coil is configured to transcutaneously receive power from the energy transfer coil.

28. A method comprising:
removably attaching a first housing to a second housing containing an energy transfer coil, wherein the energy transfer coil is configured to recharge a rechargeable power source of an implantable medical device and the first housing contains a phase change material configured to absorb heat from the energy transfer coil.

29. The method of claim 28, wherein removably attaching the first housing to the second housing containing the energy transfer coil comprises rotating a threaded structure of the first housing against a threaded surface of the second housing containing the energy transfer coil until the first housing is in thermal communication with the second housing.

30. The method of claim 28, wherein removably attaching the first housing to the second housing containing the energy transfer coil comprises radially bending at least one retaining member of the first housing and disposing the second housing containing the energy transfer coil between the at least one retaining member and the first housing.

31. The method of claim 28, wherein removably attaching the first housing to the second housing containing the energy transfer coil comprises retaining the first housing and the second housing containing the energy transfer coil within an elastic sheath such that the first housing is in thermal communication with the second housing containing the energy transfer coil.

* * * * *